(12) United States Patent
Yamoaka et al.

(10) Patent No.: US 7,776,575 B2
(45) Date of Patent: Aug. 17, 2010

(54) MUTANT GLUCOSE DEHYDROGENASE

(75) Inventors: Hideaki Yamoaka, Kyoto (JP); Masashi Tsukada, Kyoto (JP)

(73) Assignee: Arkray, Inc., Kyoto-shi, Kyoto (JP)

( * ) Notice: Subject to any disclaimer, the term of this patent is extended or adjusted under 35 U.S.C. 154(b) by 0 days.

(21) Appl. No.: 12/556,142

(22) Filed: Sep. 9, 2009

(65) Prior Publication Data

US 2010/0086989 A1 Apr. 8, 2010

Related U.S. Application Data

(62) Division of application No. 11/665,296, filed as application No. PCT/JP2006/311774 on Jun. 12, 2006, now Pat. No. 7,604,969.

(30) Foreign Application Priority Data

Jun. 20, 2005 (JP) ............................. 2005-179231

(51) Int. Cl.
*C12N 9/04* (2006.01)
*C12N 1/20* (2006.01)
*C12N 15/00* (2006.01)
*C12P 21/04* (2006.01)
*C12Q 1/00* (2006.01)
*C12Q 1/32* (2006.01)
*C07H 21/04* (2006.01)
*C12M 1/00* (2006.01)
*C12Q 1/68* (2006.01)

(52) U.S. Cl. ............................... 435/190; 435/4; 435/6; 435/26; 435/69.1; 435/71.1; 435/252.3; 435/320.1; 435/440; 536/23.2; 205/777.5; 204/403.01; 204/403.1

(58) Field of Classification Search ........................ None
See application file for complete search history.

(56) References Cited

U.S. PATENT DOCUMENTS

| | | |
|---|---|---|
| 6,103,509 A | 8/2000 | Sode |
| 2004/0023330 A1 | 2/2004 | Sode |
| 2006/0019328 A1 | 1/2006 | Sode |

FOREIGN PATENT DOCUMENTS

| | | |
|---|---|---|
| EP | 1 331 272 | 7/2003 |
| EP | 1 367 120 | 12/2003 |
| EP | 1 600 503 | 11/2005 |
| EP | 1 739 174 | 1/2007 |
| JP | 2003-274964 | 9/2003 |
| WO | WO 02/34919 | 5/2002 |

OTHER PUBLICATIONS

Inose, et al., "Cloning and Expression of the Gene Encoding Catalytic Subunit of Thermostable Glucose Dehydrogenase from *Burkholderia cepacia* in *Escherichia coli*," *Biochimica et Biophysica Acta*, vol. 1645, pp. 133-138, 2003.

Sode, et al. "Elucidation of the Region Responsible for EDTA Tolerance in PQQ Glucose Dehydrogenases by constructing *Escherichia coli* and *Acinetobacter calcoaceticus* Chimeric Enzymes," *Biochemical and Biophysical Research Communications*, vol. 211, No. 1, pp. 268-273, Jun. 6, 1995.

Yoshida, et al. "Engineering a Chimeric Pyrroloquinoline Quinone Glucose Dehydrogenase: Improvement of EDTA Tolerance, Thermal Stability and Substrate Specificity," *Protein Engineering*, vol. 12, No. 1, p. 63-70, 1999.

Branden, et al. *Introduction to Protein Structure*, Garland Publishing, Inc., New York, p. 247, 1991.

*Primary Examiner*—Yong D Pak
(74) *Attorney, Agent, or Firm*—Knobbe, Martens, Olson & Bear, LLP

(57) ABSTRACT

A mutant glucose dehydrogenase having the amino acid sequence of SEQ ID NO: 3 or an amino acid sequence of SEQ ID NO: 3 including substitution, deletion, insertion or addition of one or more amino acid residues other than the amino acid residue at the 365th position and having glucose dehydrogenase activity, wherein an amino acid residue at a position corresponding to the 365th position of the amino acid sequence is replaced with another amino acid residue, and the mutant glucose dehydrogenase shows an improved substrate specificity to glucose.

25 Claims, 5 Drawing Sheets

MUTANT GLUCOSE DEHYDROGENASE

RELATED APPLICATIONS

This application is a divisional of U.S. application Ser. No. 11/665,296, filed Apr. 13, 2007 which is the U.S. National Phase under 35 U.S.C. §371 of International Application PCT/JP2006/311774, filed Jun. 12, 2006, which was published in a language other than English which claims priority of Japanese Application No. 2005-179231, filed Jun. 20, 2005.

TECHNICAL FIELD

The present invention relates to a mutant glucose dehydrogenase showing improved substrate specificity. The mutant glucose dehydrogenase of the present invention can be suitably used for glucose sensors, glucose assay kits and so forth, and is useful in the fields of biochemistry, clinical medicine, and so forth.

BACKGROUND ART

In recent years, a variety of enzymes are used as biosensor elements. Glucose oxidases (GODs) have already been practically used as sensor elements for measuring blood glucose levels for the purpose of diagnosis of diabetes. However, GODs suffer from a problem that they are affected by dissolved oxygen in samples. Therefore, glucose dehydrogenases (GDHs), which are not affected by dissolved oxygen in samples, are drawing attentions as alternatives of GODs.

As GDHs, one requiring $NAD(P)^+$ as a coenzyme (E.C.1.1.1.47), one requiring pyroloquinoline quinone (PQQ) as a coenzyme (PQQGDH; E.C.1.1.99.17) etc. have been reported. GDH requiring $NAD(P)^+$ as a coenzyme suffers from a problem as a sensor element that $NAD(P)^+$ needs to be added to the assay system. On the other hand, it is unnecessary for coenzyme-binding type GDHs such as PQQGDH to add a coenzyme to the assay system.

Further, sensor elements are desired to exhibit a stability that the function as a sensor is not lost even when they are continuously used or left at room temperature.

Since enzymes derived from thermophilic bacteria which grow at high temperature generally exhibit high thermostability, and high stability even in long-term storage, continuous use and so forth, application of them as sensor elements is expected. However, although GDHs derived from *Thermoplasma acidophilum* and *Sulfolobus solfataricus* have been reported as thermostable GDHs derived from thermophilic bacteria, both of them require $NAD(P)^+$ as a coenzyme.

On the other hand, thermostable GDH produced by *Burkholderia cepacia*, a moderately thermophilic bacterium, is an FAD-binding type GDH, and the enzymological characteristics thereof such as optimum reaction temperature, thermostability and substrate specificity have already been elucidated (Patent document 1). This GDH usually exists as a heterooligomer consisting of a catalytic subunit (α-subunit) showing high heat resistance, an electron transfer subunit (β-subunit), which is cytochrome C, and γ-subunit of which function is unknown, and its optimum reaction temperature is 45° C. These subunits are dissociated by a heat treatment at a temperature higher than 50° C. to release the α-subunit monomer of which optimum reaction temperature is 75° C. The α-subunit monomer is thermostable and exhibits 80% or more of residual activity even after a heat treatment at 60° C. for 30 minutes. The genes coding for these subunits have also already been isolated (Patent documents 1 and 2).

However, coenzyme-binding type GDHs generally exhibit a broad substrate specificity, and also react with maltose, galactose and so forth in addition to glucose. When they are applied as a glucose sensor for monitoring blood sugar levels of diabetic patients, and the diabetic patients have such severe symptoms that peritoneal dialysis must be performed, there is a risk that values higher than the true blood sugar levels may be obtained, because a large amount of maltose is contained in the dialysate. GDH derived from *Burkholderia cepacia* also exhibits reactivity to maltose and galactose in addition to glucose.

A technique of changing substrate specificity of GDH by introducing an amino acid substitution mutation is known. As such mutant GDHs, for example, there are known PQQGDHs derived from *E. coli* (Patent documents 3 and 4), *Acinetobacter calcoaceticus* (*Gluconobacter calcoaceticus*) (Patent document 5), and *Acinetobacter baumannii* (Patent documents 6 to 8) requiring pyroloquinoline quinone as a coenzyme.

[Patent document 1] U.S. Patent Application No. 2004/0023330

[Patent document 2] International Patent Publication WO03/091430

[Patent document 3] Japanese Patent Laid-open (Kokai) No. 10-243786

[Patent document 4] Japanese Patent Laid-open No. 2001-197888

[Patent document 5] Japanese Patent Laid-open No. 2004-173538

[Patent document 6] Japanese Patent Laid-open No. 2004-313172

[Patent document 7] Japanese Patent Laid-open No. 2004-313180

[Patent document 8] Japanese Patent Laid-open No. 2004-344145

DISCLOSURE OF THE INVENTION

An object of the present invention is to provide an FAD-binding type GDH showing an improved substrate specificity to glucose.

The inventors of the present invention conducted various researches in order to achieve the foregoing object. As a result, they found that by modifying the amino acid sequence of the FAD-binding type GDH derived from *Burkholderia cepacia* at a specific site, the reactivity thereof to sugars other than glucose could be decreased while maintaining the reactivity to glucose, and thus accomplished the present invention.

That is, the present invention provides the followings.

(1) A mutant glucose dehydrogenase having the amino acid sequence of SEQ ID NO: 3 or an amino acid sequence of SEQ ID NO: 3 including substitution, deletion, insertion or addition of one or more amino acid residues other than the amino acid residue at the 365th position and having glucose dehydrogenase activity, wherein an amino acid residue at a position corresponding to the 365th position of the amino acid sequence is replaced with another amino acid residue, and the mutant glucose dehydrogenase shows an improved substrate specificity to glucose.

(2) The mutant glucose dehydrogenase according to (1), which has the amino acid sequence of SEQ ID NO: 3 except for a position corresponding to the 365th position.

(3) The mutant glucose dehydrogenase according to (1) or (2), which shows a reduced reactivity to a disaccharide compared with a glucose dehydrogenase having a wild type amino acid residue at a position corresponding to the 365th position.

(4) The mutant glucose dehydrogenase according to (3), wherein the disaccharide is maltose.

(5) The mutant glucose dehydrogenase according to (4), which shows a reactivity to maltose in a degree of 20% or less of reactivity to glucose.

(6) The mutant glucose dehydrogenase according to any one of (1) to (5), wherein the other amino acid residue is an amino acid residue selected from phenylalanine, tyrosine, tryptophan and histidine residues.

(7) The mutant glucose dehydrogenase according to any one of (1) to (6), wherein amino acid residue or residues corresponding to at least one position selected from the 324th, 326th, 333rd, 334th, 368th, 369th, 376th, 377th, 418th, 419th, 436th, 433rd, 448th, 472nd, 475th, 525th and 529th positions in the amino acid sequence of SEQ ID NO: 3 are replaced with another or other amino acid residues.

(8) The mutant glucose dehydrogenase according to (7), wherein the position consists of at least one position selected from the 326th, 472nd, 475th and 529th positions.

(9) The mutant glucose dehydrogenase according to (8), wherein the position is the 472nd position.

(10) The mutant glucose dehydrogenase according to (8), wherein the position is the 475th position.

(11) The mutant glucose dehydrogenase according to (8), wherein the position consists of both the 472nd position and the 475th position.

(12) The mutant glucose dehydrogenase according to (8), wherein the position is the 326th position.

(13) The mutant glucose dehydrogenase according to (8), wherein the position is the 529th position.

(14) The mutant glucose dehydrogenase according to (9), wherein an amino acid residue at a position corresponding to the 472nd position is replaced with an amino acid residue selected from aspartic acid, glutamic acid, phenylalanine, tyrosine, isoleucine, asparagine and histidine residues.

(15) The mutant glucose dehydrogenase according to (10), wherein an amino acid residue at a position corresponding to the 475th position is replaced with histidine or serine residue.

(16) The mutant glucose dehydrogenase according to (12), wherein an amino acid residue corresponding to the 326th serine is replaced with glutamine or valine residue.

(17) The mutant glucose dehydrogenase according to (13), wherein an amino acid residue corresponding to the 529th leucine is replaced with tyrosine, histidine or tryptophan residue.

(18) A mutant glucose dehydrogenase having the amino acid sequence of SEQ ID NO: 3 or an amino acid sequence of SEQ ID NO: 3 including substitution, deletion, insertion or addition of one or more amino acid residues and having glucose dehydrogenase activity, which includes (i) substitution of other amino acid residue or residues for a residue or residues at a position or positions corresponding to at least one position selected from the 324th, 326th, 333rd, 334th, 365th, 368th, 369th, 376th, 377th, 418th, 419th, 436th, 433rd, 448th, 525th and 529th positions in the amino acid sequence of SEQ ID NO: 3, (ii) substitution of aspartic acid residue for an amino acid residue at a position corresponding to the 472nd position, and (iii) substitution of histidine residue for an amino acid residue at a position corresponding to the 475th position, and shows improved substrate specificity to glucose.

(19) The mutant glucose dehydrogenase according to (18), wherein the other amino acid residue or residues are selected from phenylalanine, tyrosine and tryptophan residues.

(20) The mutant glucose dehydrogenase according to (18), wherein the position is the 326th position, and an amino acid residue at a position corresponding to the position is replaced with glutamine or valine residue.

(21) The mutant glucose dehydrogenase according to (18), wherein the position is the 529th position, and an amino acid residue at a position corresponding to the position is replaced with tyrosine, histidine or tryptophan residue.

(22) An FAD-binding type mutant glucose dehydrogenase containing the amino acid sequence of SEQ ID NO: 7.

(23) A mutant glucose dehydrogenase complex containing at least the mutant glucose dehydrogenase according to any one of (1) to (22) and an electron transfer subunit.

(24) The glucose dehydrogenase complex according to (23), wherein the electron transfer subunit is cytochrome C.

(25) A DNA coding for the mutant glucose dehydrogenase according to any one of (1) to (22).

(26) A microorganism harboring the DNA according to (25) and producing the mutant glucose dehydrogenase according to any one of (1) to (22) or the mutant glucose dehydrogenase complex according to (23).

(27) A glucose assay kit comprising the mutant glucose dehydrogenase according to (1) to (22), the mutant glucose dehydrogenase complex according to (23), or the microorganism according to (26).

(28) A glucose sensor comprising the mutant glucose dehydrogenase according to (1) to (22), the mutant glucose dehydrogenase complex according to (23), or the microorganism according to (26).

BEST MODE FOR CARRYING OUT THE INVENTION

Figure 1:
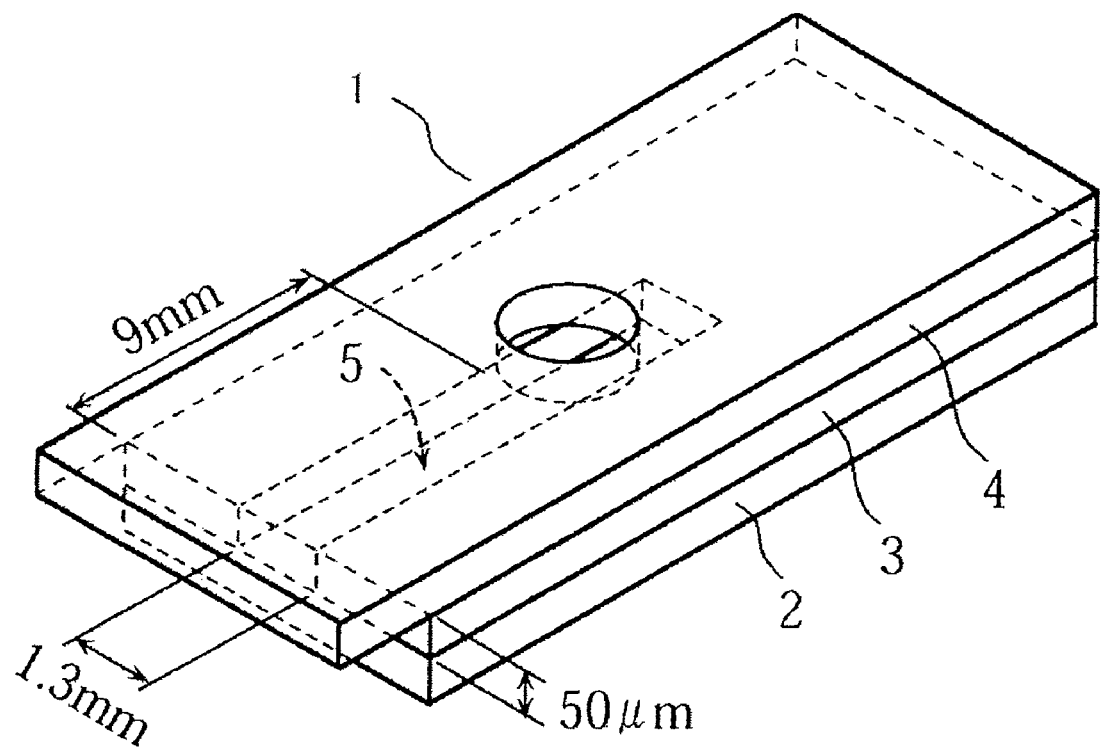
FIG. 1 shows structure of a glucose sensor.

Hereafter, the present invention will be explained in detail. The mutant GDH of the present invention is produced by introducing a specific mutation into a wild type GDH. Examples of the wild type GDH include GDHs produced by *Burkholderia cepacia*. Examples of the GDHs produced by *Burkholderia cepacia* include GDHs produced by the *Burkholderia cepacia* KS1, JCM2800 and JCM2801 strains. The KS1 strain was deposited at the independent administrative corporation, National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Sep. 25, 2000 and given an accession number FERM BP-7306. The JCM2800 and JCM2801 strains are stored at the independent administrative corporation, RIKEN, Bioresource Center, Japan Collection of Microorganisms (JCM).

The nucleotide sequence of a chromosomal DNA fragment containing the GDH α-subunit gene and a part of the β-subunit gene of the KS1 strain is shown in SEQ ID NO: 1 (U.S. Patent Application No. 2004/0023330). Three open reading frames (ORF) exist in this nucleotide sequence, the second and third ORFs from the 5' end side code for the α-subunit (SEQ ID NO: 3) and the β-subunit (SEQ ID NO: 4), respectively. Further, it is inferred that the first ORF codes for the γ-subunit (SEQ ID NO: 2). Further, the nucleotide sequence of a fragment containing the full-length β-subunit gene is shown in SEQ ID NO: 5. Further, the amino acid sequence of the β-subunit is shown in SEQ ID NO: 6 (EP1498484A). It is inferred that the amino acid numbers 1 to 22 in SEQ ID NO: 6 correspond to a signal peptide. Although the first amino acid residues are Val in SEQ ID NOS: 5 and 6, they are very likely to be Met and may be eliminated after translation.

The mutant GDH of the present invention may consist of the α-subunit alone, a complex comprising the α-subunit and the β-subunit, or a complex comprising the α-subunit, β-subunit and γ-subunit. The mutant GDH of the present invention is obtained by introducing a specific mutation into the α-subunit in any case, and may have a conservative mutation in addition to the above specific mutation. Further, the other subunits may be of a wild type or have a conservative mutation. The term "conservative mutation" means a mutation that does not substantially affect the GDH activity.

The mutant α-subunit of the present invention preferably has the amino acid sequence of SEQ ID NO: 3 except that it includes the specific mutation described later. Further, the mutant α-subunit may have the aforementioned conservative mutation so long as it has the GDH activity. That is, it may be a protein having an amino acid sequence of SEQ ID NO: 3 including substitution, deletion, insertion or addition of one or more amino acid residues in addition to the aforementioned specific mutation. SEQ ID NO: 3 shows an amino acid sequence that can be encoded by the nucleotide sequence of SEQ ID NO: 1. However, the methionine residue at the N-terminus may be eliminated after translation. The aforementioned term "one or several" preferably means a number of 1 to 10, more preferably 1 to 5, particularly preferably 1 to 3.

Further, the β-subunit typically has the amino acid sequence of SEQ ID NO: 6. However, so long as it functions as the β-subunit of GDH, it may be a protein having an amino acid sequence of the amino acid numbers 23 to 425 of SEQ ID NO: 6 including substitution, deletion, insertion or addition of one or more amino acid residues. The aforementioned term "one or several" preferably means a number of 1 to 20, more preferably 1 to 10, particularly preferably 1 to 5. The expression "functions as the GDH β-subunit" means to function as cytochrome C without degrading the enzymatic activity of GDH.

Specific examples of the wild type α-subunit gene include a DNA containing the nucleotide sequence corresponding to the nucleotide numbers 764 to 2380 of SEQ ID NO: 1. Further, the α-subunit gene may be a DNA having the nucleotide sequence corresponding to the nucleotide numbers 764 to 2380 in the nucleotide sequence of SEQ ID NO: 1 or a DNA which is hybridizable with a probe prepared from that sequence under a stringent condition and codes for a protein having the GDH activity.

Further, specific examples of the β-subunit gene include a DNA having the nucleotide sequence corresponding to the nucleotide numbers 187 to 1398 of SEQ ID NO: 5. Further, the β-subunit gene may be a DNA which has the nucleotide sequence corresponding to the nucleotide numbers 187 to 1398 of SEQ ID NO: 5, or a DNA which is hybridizable with a probe prepared from that sequence under a stringent condition and codes for a protein that can function as the β-subunit.

Examples of the aforementioned stringent condition include, for example, a condition under which DNAs having a homology of 70% or more, preferably 80% or more, more preferably 90% or more, particularly preferably 95% or more, hybridize with each other, and it is specifically exemplified by the condition of 1×SSC, 0.1% SDS at 60° C.

The α-subunit gene and the β-subunit gene can be obtained by, for example, PCR using chromosomal DNA of the Burkhorderia cepacia KS1 strain as a template. Primers for PCR can be prepared by chemical synthesis on the basis of the aforementioned nucleotide sequences. Further, they can also be obtained from chromosomal DNA of the Burkhorderia cepacia KS1 strain by hybridization using an oligonucleotide prepared on the basis of the aforementioned sequences as a probe. Further, variants thereof can also be similarly obtained from other strains of Burkhorderia cepacia. Examples of the other bacterial strains include the aforementioned JCM2800 and JCM2801 strains. The α-subunits of GDHs produced by these strains have homologies of 95.4 and 93.7%, respectively, to the α-subunit of the KS1 strain.

Further, GDHs produced by other microorganisms may also be used to prepare the mutant GDH of the present invention, so long as GDH having a structure and enzymatic characteristics similar to those of Burkhorderia cepacia GDH is chosen. Examples of such GDH include GDHs derived from (i) Burkholderia pseudomallei, (ii) Burkholderia mallei, and (iii) Ralstonia solanacearum ((i) and (ii): Proc. Natl. Acad. Sci. U.S.A. 101 (39), 14240-14245 (2004), (iii): Nature 415 (6871), 497-502 (2002)).

The mutant GDH of the present invention shows improved substrate specificity to glucose, because it is obtained by adding the specific mutation to such a wild type GDH or GDH having a conservative mutation as described above. The "improved substrate specificity to glucose" include reduced reactivity to other monosaccharides, disaccharides and oligosaccharides such as maltose, galactose and xylose with the substantially same reactivity to glucose, and improved reactivity to glucose compared with reactivities to other saccharides. For example, even if the reactivity to glucose is reduced, if the reactivities to other saccharides are reduced in larger degrees, the substrate specificity for glucose is improved. Moreover, even if the reactivities to other saccharides are increased, if the substrate specificity to glucose is increased in a larger degree, the substrate specificity to glucose is improved. Specifically, for example, if improvement of the substrate specificity of the mutant enzyme relative to that of a wild type enzyme (the substrate specificity is a ratio of specific activity for saccharide other than glucose such as maltose to specific activity for glucose, and the improvement is represented by the following equation) is 10% or more, preferably 20% or more, more preferably 40% or more, the substrate specificity shall be improved. For example, if the substrate specificity of a wild type enzyme is 60%, and the substrate specificity of a mutant GDH is 40%, the reactivity to other saccharides other than glucose is reduced by 33%.

Substrate specificity=(Specific activity for saccharides other than glucose/Specific activity for glucose)×100

Improvement of substrate specificity=(A−B)×100/A

A: Substrate specificity of wild type enzyme

B: Substrate specificity of mutant enzyme

Further, the reactivity (specific activity) for maltose of the mutant GDH is preferably 30% or less, more preferably 20% or less, of the reactivity (specific activity) for glucose.

Specific examples of the specific mutation include the followings.

(1) Substitution of another amino acid residue for the amino acid residue at a position corresponding to the 365th position of the amino acid sequence of SEQ ID NO: 3

(2) Substitution of another amino acid residue for the amino acid residue at a position corresponding to the 365th position of the amino acid sequence of SEQ ID NO: 3, and substitution of another or other amino acid residues for at least one or arbitrary two or more amino acid residues at position or positions corresponding to the 324th, 326th, 333rd, 334th, 368th, 369th, 376th, 377th, 418th, 419th, 436th, 433rd, 448th, 472nd, 475th, 525th and 529th positions in the amino acid sequence of SEQ ID NO: 3

(3) (i) Substitution of another or other amino acid residues for amino acid residue or residues at a position or positions corresponding to at least one or arbitrary two or more positions selected from the 324th, 326th, 333rd, 334th, 365th, 368th, 369th, 376th, 377th, 418th, 419th, 436th, 433rd, 448th, 525th and 529th positions in the amino acid sequence of SEQ ID NO: 3, (ii) substitution of another amino acid residue for an amino acid residue at a position corresponding to the 472nd position, and (iii) substitution of another amino acid residue for an amino acid residue at a position corresponding to the 475th position.

Examples of the aforementioned specific mutation further include such a mutation that the amino acid sequence of SEQ ID NO: 7 should be contained in the amino acid sequence of GDH. The amino acid sequence of SEQ ID NO: 7 corresponds to the sequence of the 360th position to the 366th position in GDH of SEQ ID NO: 3. It is considered that even if the GDH is an FAD-binding type GDH other than that of *Burkhorderia cepacia*, substrate specificity of a mutant GDH containing the amino acid sequence of SEQ ID NO: 7 should be improved, if a corresponding wild type GDH does not contain the amino acid sequence of SEQ ID NO: 7.

Examples of the other amino acid residue mentioned in the above mutation (1) include those of amino acids other than serine, specifically, phenylalanine, tyrosine, aspartic acid, histidine, arginine, tryptophan, lysine, asparagine, leucine, cysteine, threonine, isoleucine, glycine, valine, methionine, glutamine, glutamic acid, alanine and proline. Among these, residues of phenylalanine, tyrosine, tryptophan and histidine are preferred.

Examples of the other amino acid residue or residues mentioned in the above mutation (2) include amino acid residues other than the amino acid residues at those positions of a wild type GDH. Among the aforementioned positions of the amino acid substitution, the 326th position, the 472nd position, the 475th position, and the 529th position are preferred, and the 472nd position and the 475th position are more preferred. Although the amino acid residues at positions corresponding to the 472nd position and the 475th position may be independently replaced, it is more preferred that both are replaced.

The amino acid residue after the substitution at the 472nd position is preferably aspartic acid, glutamic acid, phenylalanine, tyrosine, isoleucine, asparagine or histidine residue, particularly preferably aspartic acid residue.

The amino acid residue after the substitution at the 475th position is preferably histidine or serine residue, particularly preferably histidine residue.

The amino acid residue after the substitution at the 326th position is preferably glutamine or valine residue.

The amino acid residue after the substitution at the 529th position is preferably tyrosine, histidine or tryptophan residue.

Preferred embodiments of the mutation (3) mentioned above are similar to those mentioned above.

The positions of the aforementioned amino acid substitution mutations are those in SEQ ID NO: 3, that the amino acid sequence of the wild type GDH α-subunit of the *Burkholderia cepacia* KS1 strain, and in a GDH α-subunit homologue or variant having an amino acid sequence including substitution, deletion, insertion or addition of one or more amino acid residues in the amino acid sequence of SEQ ID NO: 3 in addition to the aforementioned specific mutations, the positions are those corresponding to the positions of the aforementioned amino acid substitutions determined by alignment with the amino acid sequence of SEQ ID NO: 3. For example, in a conservative GDH α-subunit variant having deletion of one amino acid residue in the region of 1st to 364th positions, the 365th position represents the 364th position in the variant.

Preferred embodiments of the mutation in the mutant GDH of the present invention are shown below (numerals represent positions in the amino acid sequence, the amino acid residues represent amino acid residues after the substitution at the positions, and "+" means that two amino acid substitutions are simultaneously included).

(A) 365Arg, 365Asn, 365Asp, 365Cys, 365Glu, 365Gly, 365His, 365Ile, 365Leu, 365Met, 365Phe, 365Pro, 365Trp, 365Tyr, 365Val, 365Lys, 365Gln, 365Thr, 365Ala (B) 326Gln, 326Val, 326Arg (C) 529His, 529Tyr, 529Trp (D) 365Tyr+326Gln, 365Tyr+326Val, 365Tyr+326Arg, 365Tyr+472Phe, 365Tyr+472Ile, 365Tyr+472Asn, 365Tyr+472Asp, 365Tyr+472His, 365Tyr+472Leu, 365Tyr+472Ser, 365Tyr+475Ser, 365Tyr+475His, 365Phe+472Phe (E) 472Asp+475His+365Phe, 472Asp+475His+326Gln, 472Asp+475His+326Thr, 472Asp+475His+326Val, 472Asp+475His+529Trp, 472Asp+475His+529His, 472Asp+475His+529Tyr, 472Tyr+475His+365Phe, 472Tyr+475His+365His, 472Tyr+475His+326Val, 472Ile+475His+326Gln (F) 472Asp+475His+529His+326Gln, 472Asp+475His+529Trp+326Gln

The inventors of the present invention compared the amino acid sequences of the GMC oxidoreductase family enzymes using FAD as a coenzyme, sorbitol dehydrogenase of *Gluconobacter oxydans* (GenBank accession AB039821), 2-ketoglutarate dehydrogenase of *Erwinia herbicola* (GenBank accession AF068066), cellobiose dehydrogenase (CDH) of *Phanerochaete chrysosporium* (J. Mol. Biol., 315(3), 421-34 (2002)), cholesterol oxidase (COD) of *Streptomyces* species (J. Struct. Biol. 116(2), 317-9 (1996)), and glucose oxidase of *Penicillium amagasakiens* (Eur. J. Biochem. 252, 90-99 (1998)), and found a region in which the FAD-binding domain and FAD-covering lid were conserved and a region in which proline was conserved, which is an amino acid residue involved in folding of proteins. Then, they examined the possibility of improving substrate specificity by modifying sequences in the vicinity of the borders between these regions and other regions. Specifically, R53 to H73, E88 to A108, N308 to G336, K362 to A377, A391 to R497, and S509 to V539 were examined. As a result, they found some positions enabling improvement of the substrate specificity in the aforementioned regions.

A GDH α-subunit having a desired mutation can be obtained by introducing a nucleotide mutation corresponding to a desired amino acid mutation into a DNA coding for the GDH α-subunit (α-subunit gene) by site-directed mutagenesis and expressing the obtained mutant DNA by using a suitable expression system. Further, a mutant GDH complex can be obtained by expressing a DNA coding for the mutant GDH α-subunit together with a DNA coding for the β-subunit (β-subunit gene) or the β-subunit gene and a DNA coding for the γ-subunit (γ-subunit gene). For the introduction of a mutation into a DNA coding for the GDH α-subunit, a polycistronic DNA fragment coding for the GDH α-subunit, γ-subunit and β-subunit in this order may also be used.

Substrate specificities to sugars of the GDH α-subunit or the GDH complex introduced with the mutation can be determined by examining reactivities to various sugars by the methods described in the examples and comparing them with reactivities of a wild type GDH α-subunit or a wild type GDH complex.

A polycistronic DNA fragment coding for the γ-subunit, α-subunit and β-subunit in this order can be obtained by, for example, PCR using chromosomal DNA of the *Burkhorderia cepacia* KS1 strain as a template and oligonucleotides having the nucleotide sequences of SEQ ID NOS: 8 and 9 as primers (see the examples described later).

Examples of vectors used for obtaining the genes of GDH subunits, introduction of mutation, expression of the genes and so forth include vectors that function in *Escherichia* bacteria, and specific examples thereof include pTrc99A, pBR322, pUC18, pUC118, pUC19, pUC119, pACYC184, pBBR122 and so forth. Examples of the promoters used for expression of genes include lac, trp, tac, trc, $P_L$, tet, PhoA and so forth. Further, insertion of these genes into a vector and ligation of a promoter can be performed in one step by inserting the α-subunit gene or other subunit genes at a suitable site in an expression vector containing the promoter. Examples of such an expression vector include pTrc99A, pBluescript, pKK223-3 and so forth.

Further, the α-subunit gene or other subunit genes may be incorporated into chromosomal DNA of a host microorganism in an expressible form.

Examples of the method for transforming a microorganism with a recombinant vector include, for example, the competent cell method using a calcium treatment, protoplast method, electroporation and so forth.

Examples of the host microorganism include *Bacillus* bacteria such as *Bacillus subtilis*, yeast such as *Saccharomyces cerevisiae* and filamentous fungi such as *Aspergillus niger*. However, the host microorganism is not limited to these examples, and host microorganisms suitable for producing foreign proteins can be used.

The mutant α-subunit, the mutant GDH complex, and the microorganism expressing them of the present invention can be used as an enzyme electrode of a glucose sensor or a component of a glucose assay kit. A glucose sensor and glucose assay kit using the wild type GDH of *Burkhorderia cepacia* are described in U.S. Patent No. 2004/0023330A1. The mutant GDH of the present invention can also be used in a similar manner.

EXAMPLES

Hereafter, the present invention will be explained more specifically with reference to examples. However, the present invention is not limited to these examples.

Example 1

Plasmids Expressing GDH of *Burkhorderia cepacia*

As plasmids expressing GDH of *Burkhorderia cepacia*, a plasmid expressing the GDH α-subunit and γ-subunit and a plasmid expressing the α-subunit, β-subunit and γ-subunit were prepared.

<1> Plasmid Expressing GDH α-Subunit and γ-Subunit

As a plasmid expressing the α-subunit and γ-subunit, plasmid pTrc99A/γ+α described in WO02/036779 (corresponding to EP1331272A1, US2004023330A1, CN1484703A) was used. This plasmid is a plasmid obtained by inserting a DNA fragment sequentially containing the GDH γ-subunit structural gene and the α-subunit structural gene isolated from chromosomal DNA of the *Burkhorderia cepacia* KS1 strain (FERM BP-7306) into the vector pTrc99A (Pharmacia) at the NcoI/HindIII site as a cloning site thereof. The GDHγα gene in this plasmid is regulated by the trc promoter. pTrc99A/γ+α has an ampicillin resistance gene.

<2> Plasmid Expressing GDH α-Subunit, β-Subunit and γ-Subunit

A plasmid expressing the GDH α-subunit, β-subunit and γ-subunit was prepared as follows.

(1) Preparation of Chromosomal DNA from *Burkhorderia cepacia* KS1 Strain

A chromosomal gene was prepared from the *Burkhorderia cepacia* KS1 strain in a conventional manner. That is, the TL liquid medium (10 g of polypeptone, 1 g of yeast extract, 5 g of NaCl, 2 g of $KH_2PO_4$, 5 g of glucose in 1 L, pH 7.2) was used, and cells of the strain was shaken overnight in the medium at 34° C. The grown cells were collected by centrifugation. The cells were suspended in a solution containing 10 mM NaCl, 20 mM Tris-HCl (pH 8.0), 1 mM EDTA, 0.5% SDS and 100 µg/ml of proteinase K and treated at 50° C. for 6 hours. To the mixture was added an equal volume of phenol-chloroform, and the mixture was stirred at room temperature for 10 minutes. Then, the supernatant was collected by centrifugation. To the supernatant was added sodium acetate at a final concentration of 0.3 M, and 2-fold volume of ethanol was overlaid to precipitate chromosomal DNA in the intermediate layer. The DNA was collected with a glass rod, washed with 70% ethanol, and then dissolved in a suitable volume of TE buffer to obtain a chromosomal DNA solution.

(2) Preparation of DNA Fragment Coding for GDH γ-Subunit, α-Subunit and β-Subunit A DNA fragment coding for the GDH γ-subunit, α-subunit and β-subunit was amplified by PCR using the aforementioned chromosomal DNA as a template and oligonucleotides having the following sequences as primers.

```
[Forward primer]
                                           (SEQ ID NO: 8)
5'-CATGCCATGGCACACAACGACAACAC-3'

[Reverse primer]
                                           (SEQ ID NO: 9)
5'-GTCGACGATCTTCTTCCAGCCGAACATCAC-3'
```

The C-terminus side of the amplified fragment was blunt-ended, the N-terminus side was digested with NcoI, and the fragment was ligated to similarly treated pTrc99A (Pharmacia). *E. coli* DH5α was transformed with the obtained recombinant vector, and colonies grown on the LB agar medium containing 50 μg/mL of ampicillin were collected. The obtained transformants were cultured in the liquid LB medium, plasmids were extracted, and DNA fragments inserted in the plasmids were analyzed. As a result, an inserted fragment of about 3.8 kb was confirmed. This plasmid was designated as pTrc99Aγαβ. The structural genes of GDH in this plasmid are regulated by the trc promoter. pTrc99Aγαβ has an ampicillin resistance gene and a kanamycin resistance gene.

Example 2

Search of Substrate Interaction Site of GDH αSubunit by Mutagenesis in GDH α-Subunit (1) Mutagenesis at 472nd Position and 475th Position The GDH α-subunit gene contained in pTrc99Aγαβ obtained in Example 1 was mutagenized so that histidine residue and asparagine residue should substitute for the 472th alanine residue and the 475th aspartic acid residue in the α-subunit encoded by the gene, respectively. This mutant is called 472D+475H mutant. It had already been confirmed by the inventors of the present invention that the substrate characteristics were improved by such mutation.

Specifically, a commercially available site-directed mutagenesis kit (Stratagene, QuikChangeII Site-Directed Mutagenesis Kit) was used to substitute codon of aspartic acid (GAT) or glutamic acid (GAA) for the codon of 475th asparagine (AAT) in the GDH α-subunit gene contained in the plasmids pTrc99A/γ+α and pTrc99Aγαβ described in Example 1. The following oligonucleotides were used as primers.

[Primer for introducing A472D mutation]
Forward primer:
                                            SEQ ID NO: 224
5'-CGTGTTCAACGACGAATTCGATCCGAACAATCACATCACGG-3'

Reverse primer:
                                            SEQ ID NO: 225
5'-CCGTGATGTGATTGTTCGGATCGAATTCGTCGTTGAACACG-3'

[Primer for introducing N475H mutation]
Forward primer:
                                            SEQ ID NO: 226
5'-AATTCGCGCCGAACCACCACATCACGGGCTC-3'

Reverse primer:
                                            SEQ ID NO: 227
5'-GAGCCCGTGATGTGGTGGTTCGGCGCGAATT-3'

(2) Mutagenesis at Position Other than 472nd Position and 475th Position

The mutant gene coding for the 472D+475H mutant obtained above was used to attain substitution of phenylalanine residue for amino acid residues in the regions shown below. However, amino acid substitution was not performed for the positions for which the wild type had phenylalanine residue as the amino acid residue. The numerals used below indicate positions in the amino acid sequence, and the alphabets before the numerals indicate kinds of amino acids. For example, R53 represents arginine at the 53rd position.

(i) R53 to H73
(ii) E88 to A108
(iii) N308 to G336
(iv) K362 to A377
(v) A391 to R497
(vi) S509 to V539

As the α-subunit gene as a target of the mutagenesis, the 472D+475H mutant for which substrate characteristic improving effect was already confirmed was used aiming at obtaining synergistic effect by the combination of mutations.

The sequences of the forward primers used for the aforementioned amino acid residue substitution are shown below. Completely complementary strands of the forward primers were used as the sequences of the reverse primers.

In the notations of mutations, the numerals indicate positions in the amino acid sequence, the alphabets before the numerals indicate kinds of amino acids before the amino acid substitution, and the alphabets after the numerals indicate amino acid residues after the amino acid substitution. For example, R53F represents substitution of phenylalanine for arginine at the 53rd position.

PCR was performed by using the following reaction composition. After a reaction at 95° C. for 30 seconds, a cycle of reactions at 95° C. for 30 seconds, 55° C. for 1 minute and 68° C. for 8 minutes was repeated 15 times. Then, after a reaction at 68° C. for 30 minutes, the reaction mixture was maintained at 4° C.

[Composition of Reaction Mixture]

| [Composition of reaction mixtrure] | |
|---|---|
| Template DNA (5 ng/μl) | 2 μl |
| (472D + 475H introduced pTrc99A/γ + α and pTrc99Aγαβ) | |
| 10 x Reaction buffer | 5 μl |
| Forward primer (100 ng/μl) | 1.25 μl |
| Reverse primer (100 ng/μl) | 1.25 μl |
| dNTP | 1 μl |
| Distilled water | 38.5 μl |
| DNA polymerase | 1 μl |
| Total | 50 μl |

After PCR, 0.5 μl of DNA polymerase I was added to the reaction mixture, and the mixture was incubated at 37° C. for 1 hour to decompose the template plasmid.

Competent cells of *Escherichia coli* DH5α (supE44, ΔlacU169(φ801acZΔM15), hsdR17, recAi, endA1, gyrA96, thi-1, relA1) were transformed with the obtained reaction mixture. Plasmids DNA were prepared from several colonies grown on the LB agar medium (1% Bacto tryptone, 0.5% yeast extract, 1% sodium chloride, 1.5% agar) containing ampicillin (50 μg/ml) and kanamycin (30 μg/ml), and sequence analysis was performed to confirm that the objective mutations had been introduced into the GDH α-subunit gene.

TABLE 1

| Primers for substitution in R53-H73 region | |
|---|---|
| Amino acid substitution | SEQ ID NO |
| R53F | 10 |
| N54F | 11 |
| Q55F | 12 |
| P56F | 13 |

TABLE 1-continued

Primers for substitution in R53-H73 region

| Amino acid substitution | SEQ ID NO |
|---|---|
| D57F | 14 |
| K58F | 15 |
| M59F | 16 |
| D60F | 17 |
| M62F | 18 |
| A63F | 19 |
| P64F | 20 |
| Y65F | 21 |
| P66F | 22 |
| S67F | 23 |
| S68F | 24 |
| P69F | 25 |
| W70F | 26 |
| A71F | 27 |
| P72F | 28 |
| H73F | 29 |

TABLE 2

Primers for substitution in E88-A108 region

| Amino acid substitution | SEQ ID NO |
|---|---|
| E88F | 30 |
| H89F | 31 |
| K90F | 32 |
| N92F | 33 |
| S93F | 34 |
| Q94F | 35 |
| Y95F | 36 |
| I96F | 37 |
| R97F | 38 |
| A98F | 39 |
| V99F | 40 |
| G100F | 41 |
| G101F | 42 |
| T102F | 43 |
| T103F | 44 |
| W104F | 45 |
| H105F | 46 |
| W106F | 47 |
| A107F | 48 |
| A108F | 49 |

TABLE 3

Primers for substitution in N308-G336 region

| Amino acid substitution | SEQ ID NO |
|---|---|
| N308F | 50 |
| S309F | 51 |
| S310F | 52 |
| D311F | 53 |
| M312F | 54 |
| V313F | 55 |
| G314F | 56 |
| R315F | 57 |
| N316F | 58 |
| L317F | 59 |
| M318F | 60 |
| D319F | 61 |
| H320F | 62 |
| P321F | 63 |
| G322F | 64 |
| T323F | 65 |
| G324F | 66 |
| V325F | 67 |

TABLE 3-continued

Primers for substitution in N308-G336 region

| Amino acid substitution | SEQ ID NO |
|---|---|
| S326F | 68 |
| Y328F | 69 |
| A329F | 70 |
| S330F | 71 |
| E331F | 72 |
| K332F | 73 |
| L333F | 74 |
| W334F | 75 |
| P335F | 76 |
| G336F | 77 |

TABLE 4

Primers for substitution in K362-I377-region

| Amino acid substitution | SEQ ID NO |
|---|---|
| I362F | 78 |
| H363F | 79 |
| L364F | 80 |
| S365F | 81 |
| N366F | 82 |
| L367F | 83 |
| S368F | 84 |
| R369F | 85 |
| I370F | 86 |
| D371F | 87 |
| Q372F | 88 |
| E373F | 89 |
| T374F | 90 |
| Q375F | 91 |
| K376F | 92 |
| I377F | 93 |

TABLE 5

Primers for substitution in A391-Y453 region

| Amino acid substitution | SEQ ID NO |
|---|---|
| A391F | 94 |
| Q392F | 95 |
| I393F | 96 |
| R394F | 97 |
| D395F | 98 |
| R396F | 99 |
| S397F | 100 |
| A398F | 101 |
| R399F | 102 |
| Y400F | 103 |
| V401F | 104 |
| Q402F | 105 |
| D404F | 106 |
| C405F | 107 |
| H407F | 108 |
| E408F | 109 |
| I409F | 110 |
| L410F | 111 |
| P413F | 112 |
| E414F | 113 |
| N415F | 114 |
| R416F | 115 |
| I417F | 116 |
| V418F | 117 |
| P419F | 118 |
| S420F | 119 |
| K421F | 120 |

TABLE 5-continued

Primers for substitution in A391-Y453 region

| Amino acid substitution | SEQ ID NO |
|---|---|
| T422F | 121 |
| A423F | 122 |
| T424F | 123 |
| D425F | 124 |
| A426F | 125 |
| I427F | 126 |
| G428F | 127 |
| I429F | 128 |
| P430F | 129 |
| R431F | 130 |
| P432F | 131 |
| E433F | 132 |
| I434F | 133 |
| T435F | 134 |
| Y436F | 135 |
| A437F | 136 |
| I438F | 137 |
| D439F | 138 |
| D440F | 139 |
| Y441F | 140 |
| V442F | 141 |
| K443F | 142 |
| R444F | 143 |
| G445F | 144 |
| A446F | 145 |
| A447F | 146 |
| H448F | 147 |
| T449F | 148 |
| R450F | 149 |
| E451F | 150 |
| V452F | 151 |
| Y453F | 152 |

TABLE 6

Primers for substitution in I477-R497 region

| Amino acid substitution | SEQ ID NO |
|---|---|
| I477F | 153 |
| T478F | 154 |
| G479F | 155 |
| S480F | 156 |
| T481F | 157 |
| I482F | 158 |
| M483F | 159 |
| G484F | 160 |
| A485F | 161 |
| D486F | 162 |
| A487F | 163 |
| R488F | 164 |
| D489F | 165 |
| S490F | 166 |
| V491F | 167 |
| V492F | 168 |
| D493F | 169 |
| K494F | 170 |
| D495F | 171 |
| C496F | 172 |
| R497F | 173 |

TABLE 7

Primers for substitution in S509-V539 region

| Amino acid substitution | SEQ ID NO |
|---|---|
| S509F | 174 |
| A510F | 175 |
| T511F | 176 |
| M512F | 177 |
| P513F | 178 |
| T514F | 179 |
| V515F | 180 |
| G516F | 181 |
| T517F | 182 |
| V518F | 183 |
| N519F | 184 |
| V520F | 185 |
| T521F | 186 |
| L522F | 187 |
| T523F | 188 |
| I524F | 189 |
| A525F | 190 |
| A526F | 191 |
| L527F | 192 |
| A528F | 193 |
| L529F | 194 |
| R530F | 195 |
| M531F | 196 |
| S532F | 197 |
| D533F | 198 |
| T534F | 299 |
| L535F | 200 |
| K536F | 201 |
| K537F | 202 |
| E538F | 203 |
| V539F | 204 |

Example 3

Analysis of Substrate Specificity of Mutant GDHs

Mutant GDHs were produced by using the mutant GDH expressing plasmids obtained in Example 2, and substrate specificities thereof were examined.

(1) Culture

Each of strains of Escherichia coli DH5α introduced with each mutation was cultured overnight at 37° C. in 2 ml of the LB medium (containing 50 µg/ml of ampicillin and 30 µg/ml of kanamycin) in an L-shaped tube with shaking. These culture broths were each inoculated into 150 ml of the LB medium (containing 50 µg/ml of ampicillin and 30 µg/ml of kanamycin) contained in a 500-ml Sakaguchi flask, and the cells were cultured at 37° C. with shaking. After 3 hours from the start of culture, isopropyl-β-D-thiogalactopyranoside (IPTG) was added at a final concentration of 0.1 mM, and the cells were further cultured for 2 hours.

(2) Preparation of Crude Enzyme Samples

The cells were collected from each culture broth obtained as described above, washed, then suspended in 10 mM potassium phosphate buffer (PPB, pH 7.0) containing 1 ml of 0.2% Triton X-100 per 0.3 mg of wet cells, and disrupted by ultrasonication. This suspension was centrifuged (10000 rpm, 10 min, 4° C.) to remove the residues, then the supernatant was ultracentrifuged (50,000 r.p.m., 60 min, 4° C.), and the obtained supernatant (water-soluble fraction) was used as a crude enzyme sample. Further, this sample was purified by usual hydrophobic chromatography (column: Octyl Sepharose, Amersham Biosciences) and ion exchange chromatography (Q-Sepharose, Amersham Biosciences) to obtain a purified enzyme sample. The objective enzyme fraction was determined by using GDH activity as an index.

(3) Measurement of GDH Activity

To 8 μl of the aforementioned purified enzyme sample was added 8 μl of a reagent for measuring activity (solution obtained by adding 10 mM PPB containing 0.2% (w/v) Triton X-100 to 12 μl of 600 mM methylphenazine methosulfate (PMS) and 120 μl of 6 mM 2,6-dichlorophenol-indophenol (DCIP) to make a total volume of 480 μl). This mixture was preincubated at each reaction temperature for one minute by using an aluminum block thermostatic chamber, then 8 μl of a substrate (glucose or maltose) at each concentration or distilled water was quickly added to the mixture, and the mixture was stirred. Absorbance at 600 nm as the DCIP-originated absorption wavelength was measured by using a spectrophotometer. The final concentrations of the reagents, DCIP and PMS, were 0.06 and 0.6 mM, respectively. The final concentration of the substrate was 5 mM.

The results are shown in Tables 8 to 14. The reaction ratio of the wild type GDH was 48%.

TABLE 8

| Enzyme | U/ml (culture medium) | | Reaction ratio |
|---|---|---|---|
|  | Glucose | Maltose | Mal/Glu |
| A472D + N475H | 2.02 | 0.28 | 13.8% |
| R53F | 3.34 | 0.42 | 12.6% |
| N54F | 2.19 | 0.32 | 14.4% |
| Q55F | 1.95 | 0.24 | 12.4% |
| P56F | 2.28 | 0.37 | 16.4% |
| D57F | 2.85 | 0.42 | 14.9% |
| K58F | 1.57 | 0.20 | 12.8% |
| M59F | 1.94 | 0.29 | 14.8% |
| D60F | 2.62 | 0.36 | 13.9% |
| M62F | 0.85 | 0.16 | 19.2% |
| A63F | 0.66 | 0.12 | 18.6% |
| P64F | 1.79 | 0.30 | 16.9% |
| Y65F | 0.29 | 0.16 | 54.0% |
| P66F | 0.12 | 0.12 | 100.0% |
| S67F | 0.70 | 0.20 | 28.0% |
| S68F | 2.23 | 0.26 | 11.6% |
| P69F | 0.60 | 0.09 | 15.1% |
| W70F | 2.64 | 0.32 | 12.2% |
| A71F | 2.90 | 0.31 | 10.7% |
| P72F | 0.05 | 0.06 | 112.7% |
| H73F | 3.25 | 0.39 | 12.1% |

TABLE 9

| Enzyme | U/ml (culture medium) | | Reaction ratio |
|---|---|---|---|
|  | Glucose | Maltose | Mal/Glu |
| E88F | 1.14 | 0.16 | 16.6% |
| H89F | 1.83 | 0.28 | 17.1% |
| K90F | 1.19 | 0.14 | 14.6% |
| N92F | 1.11 | 0.17 | 18.4% |
| S93F | 2.47 | 0.38 | 16.7% |
| Q94F | 1.16 | 0.14 | 15.0% |
| Y95F | 1.89 | 0.20 | 12.5% |
| I96F | 0.53 | 0.06 | 17.7% |
| R97F | 0.73 | 0.10 | 17.6% |
| A98F | 2.47 | 0.24 | 11.0% |
| V99F | 0.40 | 0.04 | 17.4% |
| G100F | 0.07 | 0.02 | 50.3% |
| G101F | −0.02 | −0.01 | 108.3% |
| T102F | −0.02 | −0.02 | 126.7% |
| T103F | −0.03 | −0.01 | 203.0% |
| W104F | 0.52 | 0.04 | 14.4% |
| H105F | 0.01 | 0.01 | 112.7% |

TABLE 9-continued

| Enzyme | U/ml (culture medium) | | Reaction ratio |
|---|---|---|---|
|  | Glucose | Maltose | Mal/Glu |
| W106F | 0.29 | 0.03 | 20.4% |
| A107F | 0.52 | 0.03 | 12.4% |
| A108F | 0.00 | 0.00 | 104.1% |

TABLE 10

| Enzyme | U/ml (culture medium) | | Reaction ratio |
|---|---|---|---|
|  | Glucose | Maltose | Mal/Glu |
| N308F | 0.03 | 0.04 | 104.7% |
| S309F | 0.03 | 0.03 | 94.4% |
| S310F | 0.04 | 0.06 | 144.8% |
| D311F | 0.76 | 0.08 | 10.3% |
| M312F | 0.19 | 0.07 | 35.4% |
| V313F | 0.04 | 0.04 | 103.8% |
| G314F | 0.15 | 0.08 | 50.6% |
| R315F | 0.01 | 0.01 | 89.5% |
| N316F | 0.16 | 0.07 | 44.4% |
| L317F | 0.10 | 0.07 | 70.4% |
| M318F | 0.04 | 0.01 | 26.6% |
| D319F | 0.03 | 0.02 | 53.8% |
| H320F | 1.30 | 0.23 | 17.9% |
| P321F | 2.43 | 0.40 | 16.6% |
| G322F | 0.04 | 0.04 | 98.9% |
| T323F | 0.62 | 0.10 | 16.5% |
| G324F | 3.34 | 0.20 | 6.0% |
| V325F | 0.08 | 0.09 | 114.1% |
| S326F | 2.45 | 0.17 | 6.7% |
| Y328F | 0.03 | 0.03 | 97.2% |
| A329F | 0.69 | 0.09 | 12.4% |
| S330F | 0.39 | 0.07 | 17.3% |
| E331F | 1.86 | 0.17 | 9.4% |
| K332F | 0.81 | 0.10 | 12.8% |
| L333F | 3.05 | 0.26 | 8.4% |
| W334F | 4.18 | 0.29 | 7.0% |
| P335F | 0.10 | 0.02 | 22.4% |
| G336F | 0.02 | 0.00 | 0.5% |

TABLE 11

| Enzyme | U/ml (culture medium) | | Reaction ratio |
|---|---|---|---|
|  | Glucose | Maltose | Mal/Glu |
| I362F | 0.11 | 0.10 | 88.2% |
| H363F | 0.47 | 0.10 | 20.4% |
| L364F | 3.30 | 0.33 | 10.1% |
| S365F | 2.89 | 0.04 | 1.2% |
| N366F | 0.04 | 0.03 | 75.8% |
| L367F | 4.30 | 0.44 | 10.2% |
| S368F | 3.88 | 0.25 | 6.4% |
| R369F | 3.58 | 0.25 | 7.1% |
| I370F | 1.30 | 0.12 | 8.9% |
| D371F | 2.73 | 0.35 | 12.9% |
| Q372F | 3.98 | 0.36 | 8.9% |
| E373F | 1.60 | 0.21 | 12.9% |
| T374F | 1.91 | 0.18 | 9.4% |
| Q375F | 3.59 | 0.39 | 10.8% |
| K376F | 2.83 | 0.20 | 6.9% |
| I377F | 3.05 | 0.23 | 7.6% |

TABLE 12

| Enzyme | U/ml (culture medium) Glucose | Maltose | Reaction ratio Mal/Glu |
|---|---|---|---|
| A391F | 2.07 | 0.22 | 10.9% |
| Q392F | 2.21 | 0.22 | 10.2% |
| I393F | 1.76 | 0.19 | 11.1% |
| R394F | 0.73 | 0.13 | 17.4% |
| D395F | 1.39 | 0.17 | 12.0% |
| R396F | 1.20 | 0.14 | 11.9% |
| S397F | 0.75 | 0.08 | 10.8% |
| A398F | 2.11 | 0.22 | 10.3% |
| R399F | 1.98 | 0.20 | 10.1% |
| Y400F | 2.35 | 0.24 | 10.0% |
| V401F | 0.57 | 0.11 | 19.2% |
| Q402F | 0.58 | 0.07 | 12.3% |
| D404F | 0.28 | 0.08 | 29.2% |
| C405F | 0.06 | 0.06 | 104.9% |
| H407F | 0.08 | 0.06 | 67.3% |
| E408F | 0.08 | 0.08 | 97.0% |
| I409F | 0.16 | 0.04 | 25.0% |
| L410F | 0.08 | 0.07 | 85.7% |
| P413F | 0.05 | 0.04 | 72.9% |
| E414F | 1.22 | 0.15 | 12.6% |
| N415F | 0.03 | 0.04 | 119.5% |
| R416F | 0.18 | 0.03 | 17.1% |
| I417F | 0.05 | 0.05 | 86.6% |
| V418F | 2.66 | 0.19 | 7.3% |
| P419F | 1.74 | 0.10 | 5.7% |
| S420F | 0.45 | 0.04 | 8.5% |
| K421F | 0.42 | 0.06 | 15.0% |
| T422F | 1.98 | 0.18 | 9.1% |
| T424F | 2.27 | 0.26 | 11.6% |
| D425F | 0.02 | 0.02 | 124.5% |
| A426F | 1.75 | 0.19 | 10.8% |
| I427F | 1.95 | 0.25 | 12.8% |
| G428F | 0.25 | 0.14 | 56.1% |
| I429F | 0.46 | 0.06 | 12.0% |
| P430F | 0.41 | 0.05 | 11.2% |
| R431F | 1.80 | 0.16 | 8.7% |
| P432F | 0.19 | 0.11 | 56.4% |
| E433F | 1.31 | 0.14 | 10.4% |
| I434F | 0.13 | 0.05 | 41.2% |
| T435F | 1.16 | 0.13 | 11.0% |
| Y436F | 4.35 | 0.26 | 6.1% |
| A437F | 2.44 | 0.22 | 9.0% |
| I438F | 0.07 | 0.03 | 39.8% |
| D439F | 0.01 | 0.01 | 73.0% |
| D440F | 0.03 | 0.04 | 155.6% |
| Y441F | 0.03 | 0.04 | 119.5% |
| V442F | 0.01 | 0.01 | 175.0% |
| K443F | 4.64 | 0.27 | 5.9% |
| R444F | 2.41 | 0.26 | 10.8% |
| H448F | 0.87 | 0.07 | 8.3% |
| T449F | 2.47 | 0.30 | 12.0% |
| R450F | 0.04 | 0.05 | 112.7% |
| E451F | 2.15 | 0.22 | 10.0% |
| V452F | 1.17 | 0.18 | 15.3% |
| Y453F | 0.17 | 0.18 | 106.1% |

TABLE 13

| Enzyme | U/ml (culture medium) Glucose | Maltose | Reaction ratio Mal/Glu |
|---|---|---|---|
| I477F | 0.83 | 0.20 | 24% |
| T478F | 0.03 | 0.03 | 104% |
| G479F | 0.05 | 0.05 | 96% |
| S480F | 0.08 | 0.11 | 144% |
| T481F | 0.01 | 0.00 | −20% |
| I482F | 0.01 | −0.01 | −200% |
| M483F | 2.54 | 0.22 | 9% |
| G484F | 0.01 | 0.01 | 116% |

TABLE 13-continued

| Enzyme | U/ml (culture medium) Glucose | Maltose | Reaction ratio Mal/Glu |
|---|---|---|---|
| A485F | 0.05 | 0.06 | 116% |
| D486F | 0.77 | 0.10 | 14% |
| A487F | 0.10 | 0.07 | 67% |
| R488F | 0.08 | 0.07 | 88% |
| D489F | 1.57 | 0.18 | 11% |
| S490F | 0.03 | 0.04 | 149% |
| V491F | 0.05 | 0.04 | 81% |
| V492F | 0.08 | 0.08 | 109% |
| D493F | 0.05 | 0.03 | 77% |
| K494F | 1.32 | 0.26 | 20% |
| D495F | 0.10 | 0.07 | 74% |
| C496F | 0.04 | 0.07 | 150% |
| R497F | 0.19 | 0.13 | 68% |

TABLE 14

| Enzyme | U/ml (culture medium) Glucose | Maltose | Reaction ratio Mal/Glu |
|---|---|---|---|
| S509F | 0.16 | 0.04 | 24% |
| A510F | 0.20 | 0.05 | 25% |
| T511F | 0.18 | 0.04 | 20% |
| M512F | 2.18 | 0.25 | 11% |
| P513F | 3.50 | 0.35 | 10% |
| T514F | 0.01 | 0.00 | 41% |
| V515F | 0.04 | 0.03 | 78% |
| G516F | 0.02 | 0.01 | 76% |
| T517F | 0.03 | 0.02 | 83% |
| V518F | 0.02 | 0.01 | 73% |
| N519F | 0.04 | 0.03 | 78% |
| V520F | 0.02 | 0.01 | 58% |
| T521F | −0.01 | −0.01 | 168% |
| L522F | 0.01 | 0.00 | −29% |
| T523F | 0.01 | 0.00 | 24% |
| I524F | 0.01 | −0.01 | −110% |
| A525F | 3.20 | 0.24 | 7% |
| A526F | 0.02 | 0.00 | 23% |
| L527F | 0.29 | 0.10 | 34% |
| A528F | 0.00 | −0.01 | 350% |
| L529F | 3.32 | 0.30 | 9% |
| R530F | 0.40 | 0.10 | 26% |
| M531F | 0.10 | 0.04 | 42% |
| S532F | 0.00 | 0.00 | 23% |
| D533F | 0.03 | 0.01 | 27% |
| L537F | 0.45 | 0.10 | 22% |
| E538F | 3.08 | 0.52 | 17% |
| V539F | 1.52 | 0.29 | 19% |

As a result, it was found that 472D+475H+365F was an extremely effective mutation, which reduced reactivity to maltose to a level of 1%, while maintaining the reactivity to glucose.

Among mutations other than the mutation at the 365th position, mutations for substituting phenylalanine for G324, S326, L333, W334, S368, R369, K376, I377, V418, P419, Y436, K433, H448, A525 and L529 reduced the reactivity to maltose to 60% or less compared with that before the mutagenesis, and thus they were effective.

Example 4

Examination of Mutagenesis at 365th Position

From the results obtained in Example 3, it was estimated that the 365th position was a very effective position for reducing the reactivity to maltose. Therefore, it was decided to examine this position in detail.

Specifically, the substrate characteristic improving effect of single mutagenesis at the 365th position of the α-subunit gene was examined.

Mutagenesis was carried out at the 365th position of the wild type GDH α-subunit gene contained in pTrc99Aγαβ, and the substrate specificity of the mutated enzyme was evaluated. The mutagenesis was carried out in the same manner as that used in Example 2.

Forward primers for the mutagenesis were as follows. Completely complementary strands of the forward primers were used as reverse primers.

TABLE 15

Primers for substitution at S365 position

| Amino acid substitution | SEQ ID NO |
|---|---|
| S365G | 205 |
| S365A | 206 |
| S365V | 207 |
| S365L | 208 |
| S365I | 209 |
| S365M | 210 |
| S365P | 211 |
| S365F | 212 |
| S365W | 213 |
| S365T | 214 |
| S365N | 215 |
| S365Q | 216 |
| S365Y | 217 |
| S365C | 218 |
| S365K | 219 |
| S365R | 220 |
| S365H | 221 |
| S365D | 222 |
| S365E | 223 |

Example 5

Analysis of Substrate Specificity of Mutant GDHs

By using the mutant GDH expressing plasmids obtained in Example 4, mutant GDHs were prepared, and substrate specificities thereof were examined in the same manner as in Example 3. The enzymatic activity was examined by using crude enzyme samples. The specific activity for glucose, specific activity for maltose and reaction ratio (specific activity for maltose/specific activity for glucose, unit is U/ml.) of each mutant GDH are shown in Table 16. As for the substrate concentration, the evaluation was performed at 5 mM and 10 mM.

TABLE 16

| | Single mutagenesis U/ml (culture medium) | | | | | |
|---|---|---|---|---|---|---|
| | 5 mM | | | 10 mM | | |
| | Glucose | Maltose | Mal/Glc | Glucose | Maltose | Mal/Glc |
| Wild type | 2.87 | 0.77 | 26.9% | 2.52 | 1.22 | 48.2% |
| S365F | 3.02 | 0.46 | 15.4% | 4.59 | 1.00 | 21.7% |
| S365D | 2.77 | 0.41 | 14.8% | 4.73 | 0.87 | 18.4% |
| S365H | 0.90 | 0.04 | 4.3% | 1.49 | 0.12 | 8.1% |
| S365R | 1.09 | 0.08 | 6.9% | 1.96 | 0.28 | 14.1% |
| S365W | 0.47 | 0.01 | 2.3% | 1.17 | 0.02 | 2.0% |
| S365Y | 1.42 | 0.02 | 1.6% | 2.46 | 0.05 | 2.0% |
| S365G | 2.51 | 0.42 | 16.9% | 3.80 | 0.81 | 21.3% |

TABLE 16-continued

| | Single mutagenesis U/ml (culture medium) | | | | | |
|---|---|---|---|---|---|---|
| | 5 mM | | | 10 mM | | |
| | Glucose | Maltose | Mal/Glc | Glucose | Maltose | Mal/Glc |
| S365E | 0.55 | 0.04 | 7.6% | 0.98 | 0.19 | 19.2% |
| S365I | 1.00 | 0.08 | 7.6% | 1.56 | 0.16 | 10.5% |
| S365P | 0.62 | 0.06 | 9.7% | 1.29 | 0.17 | 13.3% |
| S365L | 0.97 | 0.07 | 7.4% | 1.59 | 0.19 | 11.7% |
| S365N | 1.90 | 0.23 | 12.3% | 2.92 | 0.43 | 14.8% |
| S365K | 1.61 | 0.13 | 7.9% | 2.35 | 0.26 | 10.9% |
| S365Q | 1.68 | 0.19 | 11.4% | 3.53 | 0.44 | 12.6% |
| S365M | 2.10 | 0.29 | 13.7% | 3.99 | 0.56 | 14.1% |
| S365T | 1.76 | 0.23 | 13.1% | 3.19 | 0.56 | 17.4% |
| S365A | 3.14 | 0.49 | 15.7% | 4.80 | 0.29 | 6.0% |
| S365C | 1.79 | 0.19 | 10.4% | 2.74 | 0.20 | 7.4% |
| S365V | 2.20 | 0.26 | 12.0% | 3.03 | 0.62 | 20.4% |

As a result, as for the 365th position, the substrate characteristic improving effect was observed for substitutions of all the amino acid residues of 19 types other than the substitution of serine residue in the wild type. Specifically, all the amino acid substitutions reduced the reactivity to maltose by 50% or more compared with the wild type. In particular, after the substitutions of tyrosine and tryptophan residues, the reactivity to maltose was 2% or less at both the substrate concentrations, 5 mM and 10 mM, whereas the reaction ratio of the wild type was around 40%. That is, the substitutions reduced the reactivity to maltose by 90% or more, and thus extremely significant substrate characteristic improving effects were observed.

Example 6

Examination of Combination Effect of 365th Position and Other Positions

As shown by the results of Examples 2 and 5, the effect was confirmed at least for the combinations of the mutation at the 365th position with the mutations 365F and 472D+475H, and single mutagenesis by all the amino acid substitutions only at the 365th position. Therefore, it became clear that the 365th position was an extremely highly effective position for improving the substrate characteristics. Therefore, aiming at further improvement of the substrate characteristics by combining the amino acid substitution at the 365th position and amino acid substitutions at other positions, further studies were conducted. Specifically, double mutagenesis at the 365th position and any of the 326th, 529th and 472nd positions, and triple mutagenesis at the 365th, 472nd, and 475th positions were examined.

TABLE 17

| | Double mutagenesis U/ml (culture medium) | | | | | |
|---|---|---|---|---|---|---|
| | 5 mM | | | 10 mM | | |
| | Glucose | Maltose | Mal/Glc | Glucose | Maltose | Mal/Glc |
| S365Y (single mutation) | 1.42 | 0.02 | 1.6% | 2.46 | 0.05 | 2.0% |
| S365F (single mutation) | 3.02 | 0.46 | 15.4% | 4.59 | 1.00 | 21.7% |
| 365Y + 326C | 2.56 | 0.02 | 1.0% | 3.71 | 0.06 | 1.5% |
| 365Y + 326Q | 2.28 | 0.01 | 0.6% | 3.32 | 0.03 | 1.0% |

TABLE 17-continued

Double mutagenesis U/ml (culture medium)

| | 5 mM | | | 10 mM | | |
|---|---|---|---|---|---|---|
| | Glucose | Maltose | Mal/Glc | Glucose | Maltose | Mal/Glc |
| 365Y + 326T | 1.76 | 0.02 | 1.2% | 2.64 | 0.06 | 2.3% |
| 365Y + 326V | 1.55 | 0.01 | 0.5% | 2.47 | 0.01 | 0.5% |
| 365Y + 326G | 2.36 | 0.03 | 1.4% | 3.32 | 0.09 | 2.6% |
| 365Y + 326E | 1.90 | 0.02 | 1.1% | 2.82 | 0.05 | 1.7% |
| 365Y + 326K | 2.98 | 0.06 | 2.0% | 4.22 | 0.17 | 4.0% |
| 365Y + 326Y | 1.60 | 0.02 | 1.3% | 2.33 | 0.04 | 1.8% |
| 365Y + 326H | 1.27 | 0.02 | 1.5% | 1.84 | 0.04 | 2.2% |
| 365Y + 326R | 1.84 | 0.01 | 0.8% | 2.63 | 0.03 | 1.0% |
| 365Y + 472F | 1.35 | 0.01 | 0.8% | 2.04 | 0.02 | 1.1% |
| 365F + 326T | 0.54 | 0.10 | 18.4% | 6.84 | 1.38 | 20.1% |
| 365F + 326G | 0.46 | 0.08 | 17.8% | 5.51 | 1.37 | 24.9% |
| 365F + 326E | 2.44 | 0.33 | 13.6% | 3.06 | 0.61 | 19.8% |
| 365F + 326R | 3.14 | 0.49 | 15.5% | 3.83 | 0.81 | 21.1% |
| 365F + 472F | 1.51 | 0.01 | 0.6% | 2.28 | 0.02 | 1.0% |
| 365Y + 475H | 2.07 | 0.027 | 1.0% | 3.62 | 0.044 | 1.5% |
| 365Y + 475S | 3.41 | 0.066 | 1.9% | 4.54 | 0.116 | 2.6% |
| 365Y + 472G | 2.60 | 0.064 | 2.5% | 4.76 | 0.078 | 1.6% |
| 365Y + 472I | 1.31 | 0.008 | 0.6% | 2.04 | 0.020 | 1.0% |
| 365Y + 472N | 2.19 | 0.018 | 0.8% | 3.42 | 0.052 | 1.5% |
| 365Y + 472D | 1.33 | 0.009 | 0.6% | 2.08 | 0.004 | 0.2% |
| 365Y + 472E | 2.99 | 0.068 | 2.3% | 5.27 | 0.089 | 1.7% |
| 365Y + 472R | 1.77 | 0.030 | 1.7% | 2.87 | 0.025 | 0.9% |
| 365Y + 472V | 3.19 | 0.073 | 2.3% | 5.10 | 0.095 | 1.9% |
| 365Y + 472C | 0.74 | 0.023 | 3.1% | 1.07 | 0.018 | 1.7% |
| 365Y + 472H | 1.04 | 0.002 | 0.2% | 1.63 | 0.005 | 0.3% |
| 365Y + 472L | 3.21 | 0.053 | 1.6% | 4.85 | 0.062 | 1.3% |
| 365Y + 472M | 1.17 | 0.019 | 1.6% | 1.87 | 0.029 | 1.5% |
| 365Y + 472F | 1.67 | 0.029 | 1.7% | 2.99 | 0.043 | 1.4% |
| 365Y + 472P | 0.44 | 0.080 | 18.1% | 0.72 | 0.048 | 6.7% |
| 365Y + 472S | 3.70 | 0.079 | 2.1% | 4.74 | 0.087 | 1.8% |
| 365Y + 472W | 0.84 | 0.046 | 5.5% | 1.63 | 0.044 | 2.7% |
| 365Y + 472Y | 0.98 | 0.051 | 5.2% | 1.85 | 0.042 | 2.3% |

It was found that the substrate characteristics were synergistically improved by the combinations with all the positions examined, and it became clear that the substrate characteristics could be further improved by a combination of a mutation at the 365th position and amino acid substitution at another position improving the substrate characteristics.

Example 7

Examination of Combination Effect of 472nd and 475th Positions with Other Positions From the results of Example 6, it was suggested that a combination of amino acid substitutions showing a substrate characteristic improving effect might synergistically improve the substrate characteristics.

Therefore, combination effect of a mutation at the 472 or 475th position, for which the substrate characteristic improving effect was already confirmed by the inventors of the present invention, and a mutation at a position other than the 365th position was examined.

Specifically, combinations of mutations of 472D+475H, which showed the highest substrate characteristic improving effect among the combinations of mutations at the 472nd and 475th position, and a mutation at the 326th position or the 529th position were examined. Moreover, other mutations at the 472nd and 475th positions were also examined.

TABLE 18

Triple mutagenesis U/ml (culture broth)

| | 5 mM | | | 10 mM | | |
|---|---|---|---|---|---|---|
| | Glucose | Maltose | Mal/Glc | Glucose | Maltose | Mal/Glc |
| 472D + 475H | 1.54 | 0.19 | 13% | 2.33 | 0.34 | 14% |
| +S365F | 1.33 | 0.01 | 0.7% | 2.44 | 0.02 | 0.9% |
| +S365D | 0.25 | 0.01 | 2.1% | 0.64 | 0.01 | 1.9% |
| +S365H | 0.48 | 0.01 | 1.9% | 0.85 | 0.02 | 2.5% |
| +S365R | 0.15 | 0.01 | 9.6% | 0.54 | 0.04 | 7.5% |
| +S365W | 0.30 | 0.01 | 3.0% | 0.54 | 0.03 | 4.8% |
| +S365Y | 0.97 | 0.03 | 2.9% | 1.66 | 0.08 | 5.1% |
| +S365V | 0.07 | 0.01 | 8.3% | 0.16 | 0.01 | 6.8% |
| 472Y + 475H | 1.30 | 0.06 | 4.5% | 2.06 | 0.15 | 7.3% |
| +S365F | 1.15 | 0.01 | 0.7% | 1.83 | 0.01 | 0.6% |
| +S365D | 0.27 | 0.01 | 4.9% | 0.55 | 0.05 | 9.5% |
| +S365H | 0.49 | 0.01 | 1.1% | 0.95 | 0.01 | 1.5% |
| +S365R | 0.33 | 0.02 | 5.0% | 0.83 | 0.06 | 6.9% |
| +S365W | 0.22 | 0.01 | 2.3% | 0.37 | 0.01 | 3.0% |
| +S365Y | 1.09 | 0.04 | 4.0% | 1.88 | 0.13 | 6.8% |
| +S365V | 0.79 | 0.02 | 2.0% | | | |
| 472F + 475S | 0.67 | 0.05 | 7.6% | 1.35 | 0.11 | 8.0% |
| +S365F | 0.88 | 0.06 | 6.7% | 1.19 | 0.08 | 7.1% |
| +S365D | 0.35 | 0.01 | 4.2% | 0.97 | 0.03 | 3.5% |
| +S365H | 0.04 | 0.00 | 9.7% | 0.13 | 0.00 | 3.4% |
| +S365R | 0.39 | 0.02 | 4.9% | 0.92 | 0.04 | 4.5% |
| +S365W | 0.10 | 0.00 | 2.9% | 0.24 | 0.00 | 1.3% |
| +S365Y | 0.36 | 0.01 | 4.1% | 0.56 | 0.02 | 3.0% |
| 472F + 475H + S365Y | 2.75 | 0.35 | 12.8% | 3.90 | 0.63 | 16.1% |

TABLE 19

Triple mutagenesis U/ml (culture broth)

| | 5 mM | | | 10 mM | | |
|---|---|---|---|---|---|---|
| | Glucose | Maltose | Mal/Glc | Glucose | Maltose | Mal/Glc |
| 472D + 475H | 1.54 | 0.19 | 13% | 2.33 | 0.34 | 14% |
| +326C | 1.27 | 0.03 | 2.4% | 2.08 | 0.11 | 5.2% |
| +326Q | 1.22 | 0.02 | 1.8% | 2.04 | 0.09 | 4.2% |
| +326T | 1.29 | 0.02 | 1.8% | 2.13 | 0.10 | 4.7% |
| +326V | 0.69 | 0.01 | 2.0% | 1.10 | 0.03 | 3.0% |
| +326G | 1.98 | 0.07 | 3.6% | 2.99 | 0.22 | 7.3% |
| +326L | 0.09 | 0.00 | 3.1% | 0.24 | 0.01 | 3.4% |
| +326E | 0.34 | 0.00 | 0.8% | 0.69 | 0.02 | 2.9% |
| +326I | 0.35 | 0.01 | 1.7% | 0.77 | 0.06 | 7.5% |
| +326K | 1.55 | 0.05 | 3.1% | 1.87 | 0.14 | 7.2% |
| 472D + 475H + 326Q | 1.20 | 0.02 | 1.7% | 1.87 | 0.07 | 3.9% |
| 472E + 475H + 326Q | 1.55 | 0.08 | 5.5% | 2.69 | 0.26 | 9.7% |
| 472H + 475H + 326Q | 0.10 | 0.02 | 23.6% | 0.17 | 0.06 | 32.0% |
| 472I + 475H + 326Q | 1.05 | 0.03 | 2.6% | 1.81 | 0.08 | 4.5% |
| 472L + 475H + 326Q | 2.17 | 0.15 | 6.7% | 3.41 | 0.32 | 9.3% |
| 472M + 475H + 326Q | 3.07 | 0.28 | 9.0% | 4.99 | 0.53 | 10.7% |
| 472N + 475H + 326Q | 2.45 | 0.24 | 9.7% | 4.01 | 0.57 | 14.3% |
| 472W + 475H + 326Q | 2.82 | 0.44 | 15.8% | 4.37 | 0.89 | 20.4% |
| 472Y + 475H + 326Q | 1.73 | 0.07 | 4.3% | 3.03 | 0.19 | 6.1% |
| 472D + 475H + 326V | 0.69 | 0.01 | 2.0% | 1.10 | 0.03 | 3.0% |
| 472E + 475H + 326V | 1.90 | 0.12 | 6.2% | 2.88 | 0.25 | 8.8% |
| 472H + 475H + 326V | 1.07 | 0.08 | 7.4% | 1.91 | 0.19 | 9.7% |
| 472I + 475H + 326V | 2.90 | 0.26 | 9.0% | 4.35 | 0.69 | 15.9% |
| 472L + 475H + 326V | 1.32 | 0.05 | 4.1% | 2.00 | 0.12 | 6.1% |
| 472M + 475H + 326V | 3.52 | 0.32 | 9.0% | 5.64 | 0.41 | 7.4% |
| 472N + 475H + 326V | 2.85 | 0.25 | 8.7% | 4.48 | 0.49 | 10.9% |
| 472W + 475H + 326V | 2.71 | 0.38 | 14.0% | 4.56 | 0.74 | 16.2% |
| 472Y + 475H + 326V | 0.99 | 0.01 | 1.2% | 1.79 | 0.05 | 2.5% |

TABLE 20

Triple mutagenesis U/ml (culture broth)

| | 5 mM | | | 10 mM | | |
|---|---|---|---|---|---|---|
| | Glucose | Maltose | Mal/Glc | Glucose | Maltose | Mal/Glc |
| 472D + 475H | 1.54 | 0.19 | 12.5% | 2.33 | 0.34 | 14.5% |
| +529F | 2.13 | 0.29 | 13.7% | 3.11 | 0.41 | 13.3% |
| +529Y | 0.21 | 0.02 | 8.3% | 0.42 | 0.03 | 7.9% |
| +529H | 1.36 | 0.11 | 7.8% | 2.24 | 0.21 | 9.4% |
| +529W | 0.49 | 0.03 | 5.1% | 0.78 | 0.04 | 5.7% |

TABLE 21

Quadruple mutagenesis U/ml (culture broth)

| | 5 mM | | | 10 mM | | |
|---|---|---|---|---|---|---|
| | Glucose | Maltose | Mal/Glc | Glucose | Maltose | Mal/Glc |
| 472D + 475H + 529H + 326Q | 0.49 | 0.01 | 1.9% | 0.93 | 0.03 | 2.8% |
| 472D + 475H + 529W + 326Q | 0.45 | 0.02 | 4.7% | 0.72 | 0.07 | 10.1% |

The synergistic effect was also confirmed for combinations of mutations at the 472 and 475th positions and other positions. In particular, the quadruple mutagenesis at the 472nd, 475th, 326th and 529th positions showed a high reducing effect for reactivity to maltose, and it was also demonstrated by this result that the substrate characteristics could be synergistically improved by combinations of the amino acid substitutions having a substrate characteristic improving effect.

Example 7

Preparation of Purified Enzymes

Some mutant GDHs among those for which improvement of the substrate specificity was observed in Examples 5 and 6 were purified. The method was the same as that described in Example 3. Specific activities (U/mg) for glucose of the purified enzymes are shown in Table 8.

As a result, it became clear that the mutations including S365Y maintained about 90% of the specific activity for glucose, and thus they were preferred mutations from the viewpoint of glucose measurement. Moreover, it also became clear that the S326Q mutation had an effect of increasing the specific activity for glucose.

TABLE 22

| Enzyme | Specific activity |
| --- | --- |
| Wild type | 1490 U/mg-p |
| 472Y + 475H + 326V | 1547 U/mg-p |
| 365Y | 1234 U/mg-p |
| 326Q + 365Y | 1316 U/mg-p |
| 472D + 475H + 365F | 477 U/mg-p |
| 472D + 475H + 529W | 963 U/mg-p |
| 472D + 475H + 529H | 961 U/mg-p |
| 472D + 475H + 326Q | 1316 U/mg-p |
| 472D + 475H + 326V | 1157 U/mg-p |

Example 8

Preparation of Colorimetric Sensor for Measuring Blood Sugar Levels Using Mutant GDHs Colorimetric sensors for measuring blood sugar level were prepared by using the mutant GDHs obtained in Example 7.

A glucose sensor having a basic structure shown in FIG. 1 was prepared. That is, the aforementioned glucose sensor had a configuration that a transparent cover 4A (material: PET) was laminated on a transparent base plate 2A via a spacer 3, and the capillary 5A was defined by the elements 2A to 4A. The dimension of the capillary 5A was 1.3 mm×9 mm×50 μm (FIG. 1). The transparent base plate 2A and the transparent cover 4A were formed with PET having a thickness of 250 μm, and the spacer 3A was formed with a black double-sided tape.

Figure 2:
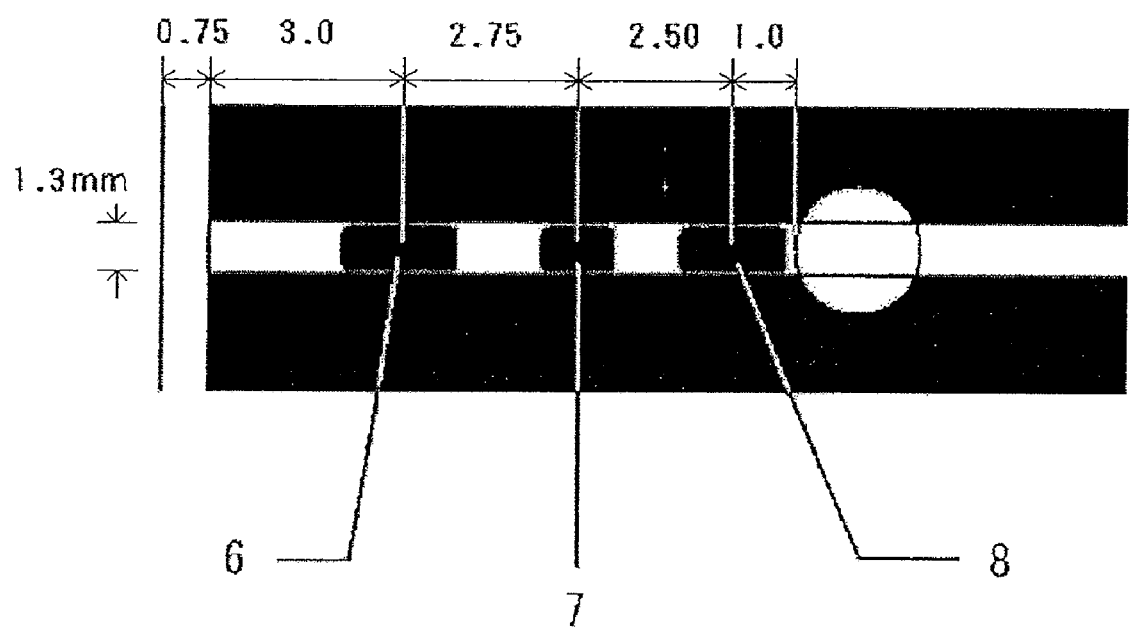
FIG. 2 shows reagent parts of a glucose sensor.

The glucose sensor had a first reagent part, a second reagent part and a third reagent part shown in FIG. 2, and ingredients and coating amounts for each part are shown in Table 23. In the table, "Ru" represents a ruthenium hexaammine complex ($Ru(NH_3)_6Cl_3$), CHAPS represents 3-[(3-cholamidopropyl)dimethylammonio]propanesulfonic acid, ACES represents N-(2-acetamido)-2-aminoethanesulfonic acid, and MTT represents 3-(4,5-dimethyl-2-thiazolyl)-2,5-diphenyl-2H-tetrazolium bromide.

TABLE 23

| First reagent part<br>Material solution for reagent part containing<br>electron transfer substance (solvent is water) | |
| --- | --- |
| Ru | Coating amount |
| 200 mM | 0.2 μl |

| Second reagent part<br>Material solution for reagent part<br>containing enzyme (solvent is water) | | | | |
| --- | --- | --- | --- | --- |
| Enzyme concentration | CHAPS | Sucrose monolaurate | ACES (pH 7.5) | Coating amount |
| 15 KU/ml | 0.20% | 0.05% | 75 mM | 0.1 μl |

TABLE 23-continued

| Third reagent part<br>Material solution for reagent part<br>containing color developer (solvent is water) | | | |
| --- | --- | --- | --- |
| MTT | Acrylamide | Methanol | Coating amount |
| 60 mM | 0.40% | 50% | 0.2 μl |

An assay sample was supplied to the capillary of the aforementioned glucose sensor, and thereafter absorbance was repeatedly measured every 0.1 second to prepare a time course of absorbance. For each measurement of absorbance, the third reagent part was irradiated with light along the direction of the height of the capillary, and upon the irradiation, light that transmitted through the glucose sensor was received. The light irradiation was attained by irradiation with light of 630 nm using a light-emitting diode. The transmitted light was received with a photodiode.

Figure 3:
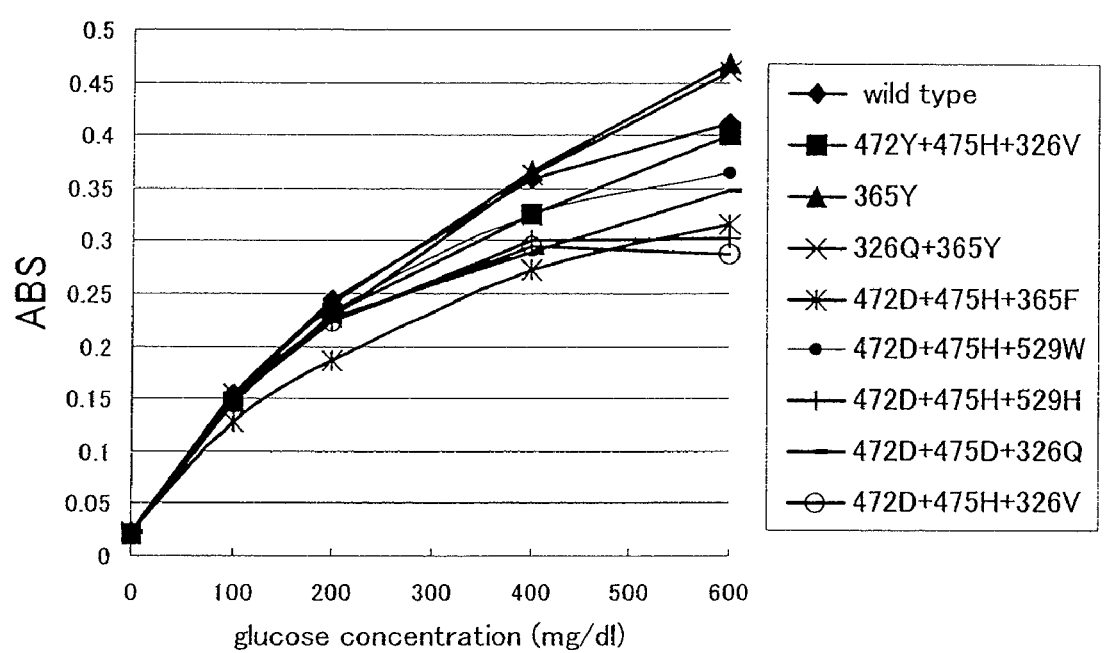
FIG. 3 shows a graph representing reactivity of a glucose sensor using a mutant GDH for glucose.

As the assay sample, blood added with glucose was used. Blood samples of which hematocrit was adjusted to 42% were added with glucose at concentrations of 0, 100, 200, 400, 600 and 800 mg/dl and used to evaluate linearity of the glucose sensor. The linearity was evaluated by plotting absorbance values at endpoints 5 seconds after the introduction of the assay samples into the sensor. The results are shown in FIG. 3.

Figure 4:
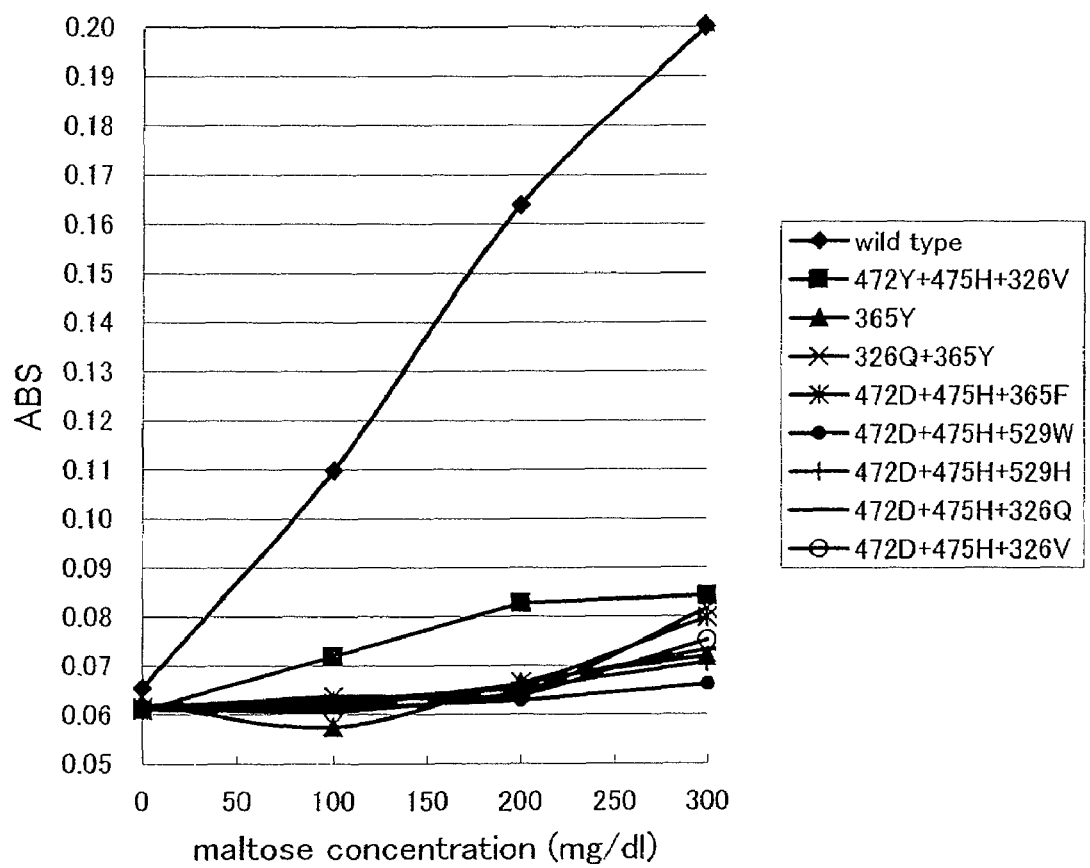
FIG. 4 shows a graph representing reactivity of a glucose sensor using a mutant GDH for maltose in the presence of glucose.

Further, blood samples of which hematocrit was adjusted to 45% and glucose concentration was adjusted to 45 mg/dl were further added with maltose at concentrations of 0, 100, 200 and 300 mg/dl, and used to evaluate influence of maltose. The results are shown in FIG. 4. The linearity was evaluated by plotting absorbance values at endpoints 5 seconds after the introduction of the assay samples also in this test.

When the linearity was evaluated by using glucose as the substrate, the absorbance increased in a concentration-dependent manner with all the enzymes, and it can be seen that glucose can be measured. In particular, the mutant GDHs including the mutation 365Y or 326Q365Y, which is a mutation including a mutation at the 365th position, showed improved linearity compared with that shown by the wild type, and thus it is suggested that they enables the measurement up to a higher concentration (around 600 mg/dl).

Figure 5:
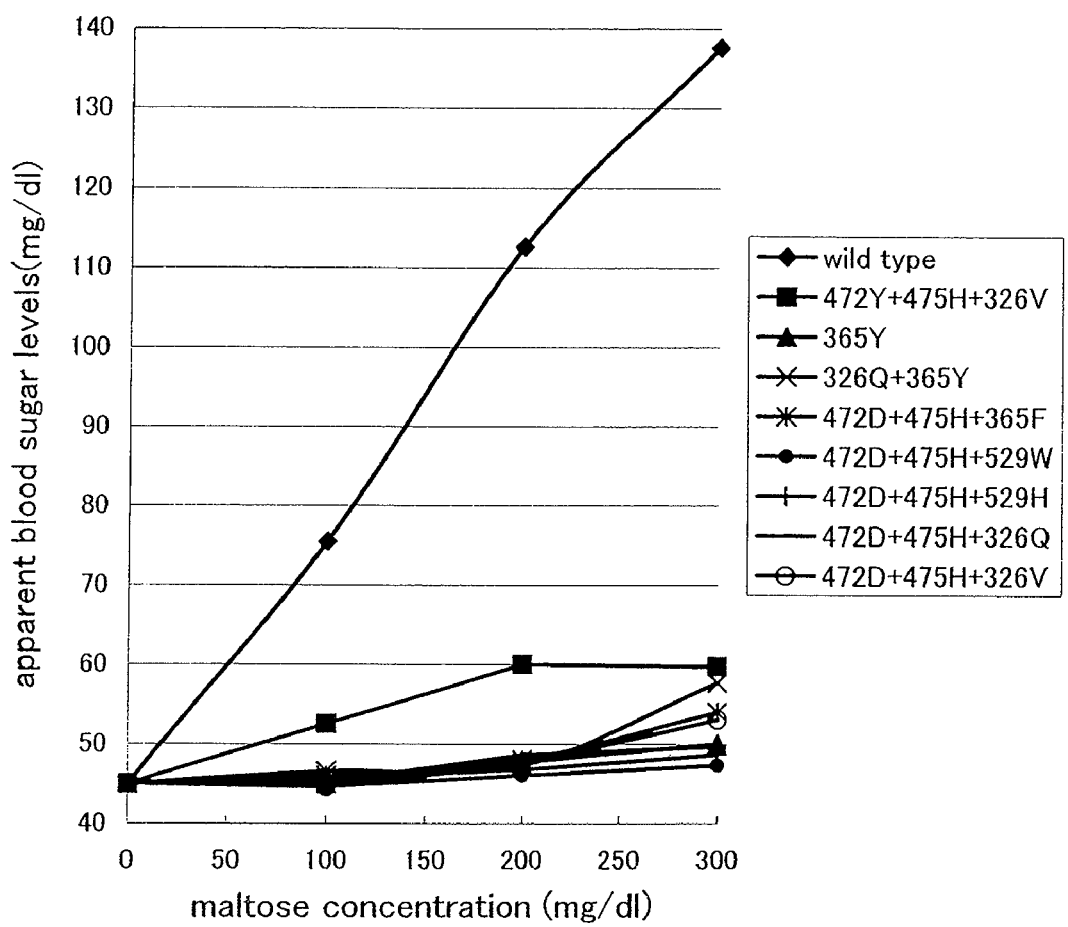
FIG. 5 shows a graph showing apparent blood sugar levels measured by using glucose sensors using a wild type GDH or a mutant GDH.

As for the influence of maltose, when maltose was added to the samples containing 45 mg/dl of glucose, absorbance increased in a maltose concentration-dependent manner with the wild type, which suggested strong reaction with maltose. On the other hand, with the sensors using the mutant enzymes, the maltose concentration-dependent increase of the absorbance was suppressed, showing less influence of maltose. The results obtained by converting these data into apparent blood sugar elevation values are shown in FIG. 5 and Table 24. In the sensor using the wild type enzyme, a hypoglycemic level (45 mg/dl of glucose) was apparently indicated as a normal value (138 mg/dl of glucose) due to contamination of maltose. On the other hand, in the sensors using the modified GDHs, the apparent blood sugar level elevated to only 60 mg/dl at most, even when the sample is contaminated with up to 300 mg/dl of maltose, and thus it can be said that the influence was significantly suppressed. In conclusion, it is suggested that mutations including a mutation at the 365th position are the most suitable in view of reactivity to glucose (linearity) and influence of maltose.

TABLE 24

| Maltose addition | Wild type | 365Y | 326Q + 365Y | 472D + 475H + 365F | 472Y + 475H + 326V |
|---|---|---|---|---|---|
| 0 | 45 | 45 | 45 | 45 | 45 |
| 100 | 75 | 45 | 47 | 46 | 53 |
| 200 | 113 | 48 | 47 | 48 | 60 |
| 300 | 138 | 50 | 58 | 54 | 60 |

| Maltose addition | 472D + 475H + 529W | 472D + 475H + 529H | 472D + 475H + 326Q | 472D + 475H + 326V |
|---|---|---|---|---|
| 0 | 45 | 45 | 45 | 45 |
| 100 | 45 | 46 | 45 | 45 |
| 200 | 46 | 47 | 49 | 47 |
| 300 | 47 | 49 | 50 | 53 |

*Unit: mg/dl

As clearly seen from the above results, in the glucose sensors using the mutant GDHs, reactivity to maltose was significantly decreased even though the linearity was maintained to an extent comparable to or hither than that of the wild type. It can be said that if these glucose sensors using the mutant GDHs are used, erroneous values are not observed at the upper limit of blood maltose level administered at hospitals or the like, 200 mg/dl, and even at 300 mg/dl higher than the upper limit, a hypoglycemic value (50 mg/dl or less) is not judged as a normal value or hyperglycemic level, and thus safe therapeutic treatment can be conducted. Further, since GDHs do not react with dissolved oxygen as described above, accurate diagnosis and treatment of diabetic patients can be conducted by providing sensors using these mutant GDHs.

Example 9

Evaluation of Purified Enzymes Based on SV Plot

SV plots were obtained for the 365Y and 326Q+365Y mutated GDHs, for which substrate specificity improving effect was observed in Examples 5 and 6, as purified enzymes.

As a result, it was confirmed that the reaction ratios (specific activity for maltose/specific activity for glucose) of the purified enzymes were also became markedly lower than that of the wild type and thus improved at all the examined substrate concentrations. Further, since the results were substantially consistent with the measurement results obtained by using the crude enzyme solutions, sufficient feasibility for evaluation of modified enzymes using crude enzymes could be confirmed. In addition, since the blood maltose level elevates up to 200 mg/dl even at most, attentions were paid particularly to the reaction ratios at the substrate concentrations of 10 mM (360 mg/dl) and 5 mM (180 mg/dl). As a result, the maltose/glucose reaction ratio of the S365Y mutated GDH was 0.1% in this concentration range, and thus it was suggested that it hardly reacted with maltose.

Moreover, it also became clear that use of the mutation 326Q in addition to the mutation 365Y can increase the specific activity for glucose, and relatively decrease the reactivity to maltose.

TABLE 25

Evaluation of enzymatic characteristics

|  | 40 | 20 | 10 | 5 | 2.5 | 1.25 | 0.625 | mM |
|---|---|---|---|---|---|---|---|---|
| specific activity for glucose | | | | | | | | |
| wild type | 1543.7 | 1490.0 | 1388.1 | 1223.4 | 925.1 | 604.6 | 346.2 | U/mg-p |
| 365Y | 1464.4 | 1234.0 | 970.8 | 661.1 | 397.2 | 218.2 | 101.8 | U/mg-p |
| 326Q365Y | 1525.8 | 1316.0 | 1022.4 | 686.4 | 436.8 | 238.8 | 114.7 | U/mg-p |
| specific activity for maltose | | | | | | | | |
| wild type | 658.1 | 501.9 | 335.3 | 194.3 | 85.9 | 27.9 | 5.4 | U/mg-p |
| 365Y | 31.1 | 8.1 | 1.4 | 0.5 | 0.2 | 0.1 | 0.0 | U/mg-p |
| 326Q365Y | 31.2 | 7.2 | 1.4 | 0.3 | 0.4 | 0.0 | 0.0 | U/mg-p |
| malsose/glucose (reaction ratio) | | | | | | | | |
| wild type | 42.6% | 33.7% | 24.2% | 15.9% | 9.3% | 4.6% | 1.6% | % |
| 365Y | 2.1% | 0.7% | 0.1% | 0.1% | 0.0% | 0.1% | 0.0% | % |
| 326Q365Y | 2.0% | 0.5% | 0.1% | 0.0% | 0.1% | 0.0% | 0.0% | % |

INDUSTRIAL APPLICABILITY

The mutant GDH of the present invention has improved substrate specificity to glucose and can be suitably used for measurement of glucose using a glucose sensor or the like.

What is claimed is:

1. An isolated DNA coding for an isolated mutant glucose dehydrogenase of SEQ ID NO: 3, wherein said mutant glucose dehydrogenase consists of a replacement of the amino acid residue at position 365 with another amino acid residue, and/or consists of a substitution, deletion, insertion or addition of 1 to 10 amino acid residues other than the amino acid residue at position 365 with another or other amino acid residue at the 324th, 326th, 333rd, 334th, 368th, 369th, 376th, 377th, 418th, 419th, 436th, 433rd, 448th, 472nd, 475th, 525th or 529th positions in the amino acid sequence of SEQ ID NO: 3, wherein said mutant glucose dehydrogenase has an increased substrate specificity to glucose compared to the glucose dehydrogenase of SEQ ID NO:3.

2. A microorganism harboring the DNA according to claim 1.

3. The microorganism according to claim 2, further comprising DNA coding for an electron transfer subunit.

4. A glucose assay kit comprising the microorganism according to claim 2.

5. A glucose sensor comprising the microorganism according to claim 2.

6. A glucose assay kit comprising the microorganism according to claim 3.

7. A glucose sensor comprising the microorganism according to claim 3.

8. The DNA encoding the isolated mutant glucose dehydrogenase according to claim 1, consisting of a replacement of serine at position 365 with another amino acid.

9. The DNA encoding the isolated mutant glucose dehydrogenase according to claim 1, which has a reduced reactivity to a disaccharide compared with the glucose dehydrogenase of SEQ ID NO: 3.

10. The DNA encoding the isolated mutant glucose dehydrogenase according to claim 9, wherein the disaccharide is maltose.

11. The DNA encoding the isolated mutant glucose dehydrogenase according to claim 10, which has a reactivity to maltose in a degree of 20% or less of reactivity to glucose.

12. The DNA encoding the isolated mutant glucose dehydrogenase according to claim 1, wherein the replacement amino acid residue is an amino acid residue selected from phenylalanine, tyrosine, tryptophan and histidine residues.

13. The DNA encoding the isolated mutant glucose dehydrogenase according to claim 1, wherein at least one position selected from the 326th, 472nd, 475th and 529th positions is replaced with another or other amino acid residues.

14. The DNA encoding the isolated mutant glucose dehydrogenase according to claim 13, wherein the 472nd position is replaced with another or other amino acid residues.

15. The DNA encoding the isolated mutant glucose dehydrogenase according to claim 13, wherein the 475th position is replaced with another or other amino acid residues.

16. The DNA encoding the isolated mutant glucose dehydrogenase according to claim 13, wherein both the 472nd position and the 475th position are replaced with other amino acid residues.

17. The DNA encoding the isolated mutant glucose dehydrogenase according to claim 13, wherein the 326th position is replaced with another or other amino acid residues.

18. The DNA encoding the isolated mutant glucose dehydrogenase according to claim 13, wherein the 529th position is replaced with another or other amino acid residues.

19. The DNA encoding the isolated mutant glucose dehydrogenase according to claim 14, wherein the amino acid residue at a position corresponding to the 472nd position is replaced with an amino acid residue selected from aspartic acid, glutamic acid, phenylalanine, tyrosine, isoleucine, asparagine and histidine residues.

20. The DNA encoding the isolated mutant glucose dehydrogenase according to claim 15, wherein the amino acid residue at the 475th position is replaced with histidine or serine residue.

21. The DNA encoding the isolated mutant glucose dehydrogenase according to claim 17, wherein the amino acid residue of the 326th position is replaced with glutamine or valine residue.

22. The DNA encoding the isolated mutant glucose dehydrogenase according to claim 18, wherein the amino acid residue at the 529th position is replaced with tyrosine, histidine or tryptophan residue.

23. An isolated DNA encoding the isolated mutant glucose dehydrogenase of the glucose dehydrogenase having the amino acid sequence of SEQ ID NO: 3, wherein said mutant glucose dehydrogenase consists of:

(i) substitution of the amino acid residue at position 365 in the amino acid sequence of SEQ ID NO: 3, (ii) substitution of aspartic acid residue for another amino acid residue at position 472, and (iii) substitution of histidine residue for another amino acid residue at position 475, wherein said mutant glucose dehydrogenase has increased substrate specificity to glucose, compared to the glucose dehydrogenase comprising the amino acid sequence of SEQ ID NO: 3.

24. The DNA encoding the isolated mutant glucose dehydrogenase according to claim 23, wherein the other amino acid residue or residues are selected from phenylalanine, tyrosine and tryptophan residues.

25. An isolated DNA encoding an isolated FAD-binding type mutant glucose dehydrogenase comprising the amino acid sequence of SEQ ID NO: 7.

* * * * *

SEQUENCE LISTING

<160> NUMBER OF SEQ ID NOS: 227

<210> SEQ ID NO 1
<211> LENGTH: 2467
<212> TYPE: DNA
<213> ORGANISM: Burkhorderia cepacia
<220> FEATURE:
<221> NAME/KEY: CDS
<222> LOCATION: (258)..(761)
<220> FEATURE:
<221> NAME/KEY: CDS
<222> LOCATION: (764)..(2380)
<220> FEATURE:
<221> NAME/KEY: CDS
<222> LOCATION: (2386)..(2466)

<400> SEQUENCE: 1

```
aagctttctg tttgattgca cgcgattcta accgagcgtc tgtgaggcgg aacgcgacat      60
gcttcgtgtc gcacacgtgt cgcgccgacg acacaaaaat gcagcgaaat ggctgatcgt     120
tacgaatggc tgacacattg aatggactat aaaaccattg tccgttccgg aatgtgcgcg     180
tacatttcag gtccgcgccg attttgaga aatatcaagc gtggttttcc cgaatccggt     240
gttcgagaga aggaaac atg cac aac gac aac act ccc cac tcg cgt cgc       290
                  Met His Asn Asp Asn Thr Pro His Ser Arg Arg
                   1               5                   10 cac ggc gac gca gcc gca tca ggc atc acg cgg cgt caa tgg ttg caa      338
His Gly Asp Ala Ala Ala Ser Gly Ile Thr Arg Arg Gln Trp Leu Gln
             15                  20                  25 ggc gcg ctg gcg ctg acc gca gcg ggc ctc acg ggt tcg ctg aca ttg      386
Gly Ala Leu Ala Leu Thr Ala Ala Gly Leu Thr Gly Ser Leu Thr Leu
         30                  35                  40 cgg gcg ctt gca gac aac ccc ggc act gcg ccg ctc gat acg ttc atg      434
Arg Ala Leu Ala Asp Asn Pro Gly Thr Ala Pro Leu Asp Thr Phe Met
     45                  50                  55 acg ctt tcc gaa tcg ctg acc ggc aag aaa ggg ctc agc cgc gtg atc      482
Thr Leu Ser Glu Ser Leu Thr Gly Lys Lys Gly Leu Ser Arg Val Ile
 60                  65                  70                  75 ggc gag cgc ctg ctg cag gcg ctg cag aag ggc tcg ttc aag acg gcc      530
Gly Glu Arg Leu Leu Gln Ala Leu Gln Lys Gly Ser Phe Lys Thr Ala
                 80                  85                  90 gac agc ctg ccg cag ctc gcc ggc gcg ctc gcg tcc ggt tcg ctg acg      578
Asp Ser Leu Pro Gln Leu Ala Gly Ala Leu Ala Ser Gly Ser Leu Thr
             95                 100                 105 cct gaa cag gaa tcg ctc gca ctg acg atc ctc gag gcc tgg tat ctc      626
Pro Glu Gln Glu Ser Leu Ala Leu Thr Ile Leu Glu Ala Trp Tyr Leu
         110                 115                 120 ggc atc gtc gac aac gtc gtg att acg tac gag gaa gca tta atg ttc      674
Gly Ile Val Asp Asn Val Val Ile Thr Tyr Glu Glu Ala Leu Met Phe
     125                 130                 135 ggc gtc gtg tcc gat acg ctc gtg atc cgt tcg tat tgc ccc aac aaa      722
Gly Val Val Ser Asp Thr Leu Val Ile Arg Ser Tyr Cys Pro Asn Lys
140                 145                 150                 155 ccc ggc ttc tgg gcc gac aaa ccg atc gag agg caa gcc tg atg gcc      769
Pro Gly Phe Trp Ala Asp Lys Pro Ile Glu Arg Gln Ala    Met Ala
                 160                 165                     170 gat acc gat acg caa aag gcc gac gtc gtc gtc gtt gga tcg ggt gtc      817
Asp Thr Asp Thr Gln Lys Ala Asp Val Val Val Val Gly Ser Gly Val
             175                 180                 185 gcg ggc gcg atc gtc gcg cat cag ctc gcg atg gcg ggc aag gcg gtg      865
Ala Gly Ala Ile Val Ala His Gln Leu Ala Met Ala Gly Lys Ala Val
```

-continued

|  |  |  |  |
|---|---|---|---|
| | 190 | 195 | 200 |

```
atc ctg ctc gaa gcg ggc ccg cgc atg ccg cgc tgg gaa atc gtc gag      913
Ile Leu Leu Glu Ala Gly Pro Arg Met Pro Arg Trp Glu Ile Val Glu
        205                 210                 215 cgc ttc cgc aat cag ccc gac aag atg gac ttc atg gcg ccg tac ccg      961
Arg Phe Arg Asn Gln Pro Asp Lys Met Asp Phe Met Ala Pro Tyr Pro
        220                 225                 230 tcg agc ccc tgg gcg ccg cat ccc gag tac ggc ccg ccg aac gac tac     1009
Ser Ser Pro Trp Ala Pro His Pro Glu Tyr Gly Pro Pro Asn Asp Tyr
235                 240                 245                 250 ctg atc ctg aag ggc gag cac aag ttc aac tcg cag tac atc cgc gcg     1057
Leu Ile Leu Lys Gly Glu His Lys Phe Asn Ser Gln Tyr Ile Arg Ala
                255                 260                 265 gtg ggc ggc acg acg tgg cac tgg gcc gcg tcg gcg tgg cgc ttc att     1105
Val Gly Gly Thr Thr Trp His Trp Ala Ala Ser Ala Trp Arg Phe Ile
                270                 275                 280 ccg aac gac ttc aag atg aag agc gtg tac ggc gtc ggc cgc gac tgg     1153
Pro Asn Asp Phe Lys Met Lys Ser Val Tyr Gly Val Gly Arg Asp Trp
                285                 290                 295 ccg atc cag tac gac gat ctc gag ccg tac tat cag cgc gcg gag gaa     1201
Pro Ile Gln Tyr Asp Asp Leu Glu Pro Tyr Tyr Gln Arg Ala Glu Glu
        300                 305                 310 gag ctc ggc gtg tgg ggc ccg ggc ccc gag gaa gat ctg tac tcg ccg     1249
Glu Leu Gly Val Trp Gly Pro Gly Pro Glu Glu Asp Leu Tyr Ser Pro
315                 320                 325                 330 cgc aag cag ccg tat ccg atg ccg ccg ctg ccg ttg tcg ttc aac gag     1297
Arg Lys Gln Pro Tyr Pro Met Pro Pro Leu Pro Leu Ser Phe Asn Glu
                335                 340                 345 cag acc atc aag acg gcg ctg aac aac tac gat ccg aag ttc cat gtc     1345
Gln Thr Ile Lys Thr Ala Leu Asn Asn Tyr Asp Pro Lys Phe His Val
                350                 355                 360 gtg acc gag ccg gtc gcg cgc aac agc cgc ccg tac gac ggc cgc ccg     1393
Val Thr Glu Pro Val Ala Arg Asn Ser Arg Pro Tyr Asp Gly Arg Pro
                365                 370                 375 act tgt tgc ggc aac aac aac tgc atg ccg atc tgc ccg atc ggc gcg     1441
Thr Cys Cys Gly Asn Asn Asn Cys Met Pro Ile Cys Pro Ile Gly Ala
380                 385                 390 atg tac aac ggc atc gtg cac gtc gag aag gcc gaa cgc gcc ggc gcg     1489
Met Tyr Asn Gly Ile Val His Val Glu Lys Ala Glu Arg Ala Gly Ala
395                 400                 405                 410 aag ctg atc gag aac gcg gtc gtc tac aag ctc gag acg ggc ccg gac     1537
Lys Leu Ile Glu Asn Ala Val Val Tyr Lys Leu Glu Thr Gly Pro Asp
                415                 420                 425 aag cgc atc gtc gcg gcg ctc tac aag gac aag acg ggc gcc gag cat     1585
Lys Arg Ile Val Ala Ala Leu Tyr Lys Asp Lys Thr Gly Ala Glu His
                430                 435                 440 cgc gtc gaa ggc aag tat ttc gtg ctc gcc gcg aac ggc atc gag acg     1633
Arg Val Glu Gly Lys Tyr Phe Val Leu Ala Ala Asn Gly Ile Glu Thr
                445                 450                 455 ccg aag atc ctg ctg atg tcc gcg aac cgc gat ttc ccg aac ggt gtc     1681
Pro Lys Ile Leu Leu Met Ser Ala Asn Arg Asp Phe Pro Asn Gly Val
        460                 465                 470 gcg aac agc tcg gac atg gtc ggc cgc aac ctg atg gac cat ccg ggc     1729
Ala Asn Ser Ser Asp Met Val Gly Arg Asn Leu Met Asp His Pro Gly
475                 480                 485                 490 acc ggc gtg tcg ttc tat gcg agc gag aag ctg tgg ccg ggc cgc ggc     1777
Thr Gly Val Ser Phe Tyr Ala Ser Glu Lys Leu Trp Pro Gly Arg Gly
                495                 500                 505 ccg cag gag atg acg tcg ctg atc ggt ttc cgc gac ggt ccg ttc cgc     1825
```

-continued

```
Pro Gln Glu Met Thr Ser Leu Ile Gly Phe Arg Asp Gly Pro Phe Arg
            510                 515                 520 gcg acc gaa gcg gcg aag aag atc cac ctg tcg aac ctg tcg cgc atc     1873
Ala Thr Glu Ala Ala Lys Lys Ile His Leu Ser Asn Leu Ser Arg Ile
        525                 530                 535 gac cag gag acg cag aag atc ttc aag gcc ggc aag ctg atg aag ccc     1921
Asp Gln Glu Thr Gln Lys Ile Phe Lys Ala Gly Lys Leu Met Lys Pro
    540                 545                 550 gac gag ctc gac gcg cag atc cgc gac cgt tcc gca cgc tac gtg cag     1969
Asp Glu Leu Asp Ala Gln Ile Arg Asp Arg Ser Ala Arg Tyr Val Gln
555                 560                 565                 570 ttc gac tgc ttc cac gaa atc ctg ccg caa ccc gag aac cgc atc gtg     2017
Phe Asp Cys Phe His Glu Ile Leu Pro Gln Pro Glu Asn Arg Ile Val
                575                 580                 585 ccg agc aag acg gcg acc gat gcg atc ggc att ccg cgc ccc gag atc     2065
Pro Ser Lys Thr Ala Thr Asp Ala Ile Gly Ile Pro Arg Pro Glu Ile
            590                 595                 600 acg tat gcg atc gac gac tac gtg aag cgc ggc gcc gcg cat acg cgc     2113
Thr Tyr Ala Ile Asp Asp Tyr Val Lys Arg Gly Ala Ala His Thr Arg
        605                 610                 615 gag gtc tac gcg acc gcc gcg aag gtg ctc ggc ggc acg gac gtc gtg     2161
Glu Val Tyr Ala Thr Ala Ala Lys Val Leu Gly Gly Thr Asp Val Val
    620                 625                 630 ttc aac gac gaa ttc gcg ccg aac aat cac atc acg ggc tcg acg atc     2209
Phe Asn Asp Glu Phe Ala Pro Asn Asn His Ile Thr Gly Ser Thr Ile
635                 640                 645                 650 atg ggc gcc gat gcg cgc gac tcc gtc gtc gac aag gac tgc cgc acg     2257
Met Gly Ala Asp Ala Arg Asp Ser Val Val Asp Lys Asp Cys Arg Thr
                655                 660                 665 ttc gac cat ccg aac ctg ttc att tcg agc agc gcg acg atg ccg acc     2305
Phe Asp His Pro Asn Leu Phe Ile Ser Ser Ser Ala Thr Met Pro Thr
            670                 675                 680 gtc ggt acc gta aac gtg acg ctg acg atc gcc gcg ctc gcg ctg cgg     2353
Val Gly Thr Val Asn Val Thr Leu Thr Ile Ala Ala Leu Ala Leu Arg
        685                 690                 695 atg tcg gac acg ctg aag aag gaa gtc tgacc gtg cgg aaa tct act ctc   2403
Met Ser Asp Thr Leu Lys Lys Glu Val       Val Arg Lys Ser Thr Leu
    700                 705                     710 act ttc ctc atc gcc ggc tgc ctc gcg ttg ccg ggc ttc gcg cgc gcg     2451
Thr Phe Leu Ile Ala Gly Cys Leu Ala Leu Pro Gly Phe Ala Arg Ala
    715                 720                 725 gcc gat gcg gcc gat c                                               2467
Ala Asp Ala Ala Asp
730

<210> SEQ ID NO 2
<211> LENGTH: 168
<212> TYPE: PRT
<213> ORGANISM: Burkhorderia cepacia

<400> SEQUENCE: 2

Met His Asn Asp Asn Thr Pro His Ser Arg Arg His Gly Asp Ala Ala
  1               5                  10                  15

Ala Ser Gly Ile Thr Arg Arg Gln Trp Leu Gln Gly Ala Leu Ala Leu
            20                  25                  30

Thr Ala Ala Gly Leu Thr Gly Ser Leu Thr Leu Arg Ala Leu Ala Asp
        35                  40                  45

Asn Pro Gly Thr Ala Pro Leu Asp Thr Phe Met Thr Leu Ser Glu Ser
    50                  55                  60
```

```
Leu Thr Gly Lys Lys Gly Leu Ser Arg Val Ile Gly Glu Arg Leu Leu
 65                  70                  75                  80

Gln Ala Leu Gln Lys Gly Ser Phe Lys Thr Ala Asp Ser Leu Pro Gln
             85                  90                  95

Leu Ala Gly Ala Leu Ala Ser Gly Ser Leu Thr Pro Glu Gln Glu Ser
            100                 105                 110

Leu Ala Leu Thr Ile Leu Glu Ala Trp Tyr Leu Gly Ile Val Asp Asn
        115                 120                 125

Val Val Ile Thr Tyr Glu Glu Ala Leu Met Phe Gly Val Val Ser Asp
        130                 135                 140

Thr Leu Val Ile Arg Ser Tyr Cys Pro Asn Lys Pro Gly Phe Trp Ala
145                 150                 155                 160

Asp Lys Pro Ile Glu Arg Gln Ala
                165

<210> SEQ ID NO 3
<211> LENGTH: 539
<212> TYPE: PRT
<213> ORGANISM: Burkhorderia cepacia

<400> SEQUENCE: 3

Met Ala Asp Thr Asp Thr Gln Lys Ala Asp Val Val Val Val Gly Ser
  1               5                  10                  15

Gly Val Ala Gly Ala Ile Val Ala His Gln Leu Ala Met Ala Gly Lys
             20                  25                  30

Ala Val Ile Leu Leu Glu Ala Gly Pro Arg Met Pro Arg Trp Glu Ile
         35                  40                  45

Val Glu Arg Phe Arg Asn Gln Pro Asp Lys Met Asp Phe Met Ala Pro
     50                  55                  60

Tyr Pro Ser Ser Pro Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
             85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
        130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270
```

-continued

```
Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 4
<211> LENGTH: 27
<212> TYPE: PRT
<213> ORGANISM: Burkhorderia cepacia

<400> SEQUENCE: 4

Val Arg Lys Ser Thr Leu Thr Phe Leu Ile Ala Gly Cys Leu Ala Leu
  1               5                  10                  15

Pro Gly Phe Ala Arg Ala Ala Asp Ala Ala Asp
             20                  25

<210> SEQ ID NO 5
<211> LENGTH: 1441
<212> TYPE: DNA
<213> ORGANISM: Burkholderia cepacia
<220> FEATURE:
<221> NAME/KEY: CDS
<222> LOCATION: (121)..(1398)

<400> SEQUENCE: 5
tccgaacctg ttcatttcga gcagcgcgac gatgccgacc gtcggtaccg taaacgtgac     60
```

```
                                                   -continued gctgacgatc gccgcgctcg cgctgcggat gtcggacacg ctgaagaagg aagtctgacc      120 gtg cgg aaa tct act ctc act ttc ctc atc gcc ggc tgc ctc gcg ttg        168
Val Arg Lys Ser Thr Leu Thr Phe Leu Ile Ala Gly Cys Leu Ala Leu
 1               5                  10                  15 ccg ggc ttc gcg cgc gcg gcc gat gcg gcc gat ccg gcg ctg gtc aag        216
Pro Gly Phe Ala Arg Ala Ala Asp Ala Ala Asp Pro Ala Leu Val Lys
             20                  25                  30 cgc ggc gaa tac ctc gcg acc gcc atg ccg gta ccg atg ctc ggc aag        264
Arg Gly Glu Tyr Leu Ala Thr Ala Met Pro Val Pro Met Leu Gly Lys
         35                  40                  45 atc tac acg agc aac atc acg ccc gat ccc gat acg ggc gac tgc atg        312
Ile Tyr Thr Ser Asn Ile Thr Pro Asp Pro Asp Thr Gly Asp Cys Met
     50                  55                  60 gcc tgc cac acc gtg aag ggc ggc aag ccg tac gcg ggc ggc ctt ggc        360
Ala Cys His Thr Val Lys Gly Gly Lys Pro Tyr Ala Gly Gly Leu Gly
 65                  70                  75                  80 ggc atc ggc aaa tgg acg ttc gag gac ttc gag cgc gcg gtg cgg cac        408
Gly Ile Gly Lys Trp Thr Phe Glu Asp Phe Glu Arg Ala Val Arg His
                 85                  90                  95 ggc gtg tcg aag aac ggc gac aac ctg tat ccg gcg atg ccg tac gtg        456
Gly Val Ser Lys Asn Gly Asp Asn Leu Tyr Pro Ala Met Pro Tyr Val
            100                 105                 110 tcg tac gcg aag atc aag gac gac gac gta cgc gcg ctg tac gcc tac        504
Ser Tyr Ala Lys Ile Lys Asp Asp Asp Val Arg Ala Leu Tyr Ala Tyr
        115                 120                 125 ttc atg cac ggc gtc gag ccg gtc aag cag gcg ccg ccg aag aac gag        552
Phe Met His Gly Val Glu Pro Val Lys Gln Ala Pro Pro Lys Asn Glu
    130                 135                 140 atc cca gcg ctg cta agc atg cgc tgg ccg ctg aag atc tgg aac tgg        600
Ile Pro Ala Leu Leu Ser Met Arg Trp Pro Leu Lys Ile Trp Asn Trp
145                 150                 155                 160 ctg ttc ctg aag gac ggc ccg tac cag ccg aag ccg tcg cag agc gcc        648
Leu Phe Leu Lys Asp Gly Pro Tyr Gln Pro Lys Pro Ser Gln Ser Ala
                165                 170                 175 gaa tgg aat cgc ggc gcg tat ctg gtg cag ggt ctc gcg cac tgc agc        696
Glu Trp Asn Arg Gly Ala Tyr Leu Val Gln Gly Leu Ala His Cys Ser
            180                 185                 190 acg tgc cac acg ccg cgc ggc atc gcg atg cag gag aag tcg ctc gac        744
Thr Cys His Thr Pro Arg Gly Ile Ala Met Gln Glu Lys Ser Leu Asp
        195                 200                 205 gaa acc ggc ggc agc ttc ctc gcg ggg tcg gtg ctc gcc ggc tgg gac        792
Glu Thr Gly Gly Ser Phe Leu Ala Gly Ser Val Leu Ala Gly Trp Asp
    210                 215                 220 ggc tac aac atc acg tcg gac ccg aat gcg ggg atc ggc agc tgg acg        840
Gly Tyr Asn Ile Thr Ser Asp Pro Asn Ala Gly Ile Gly Ser Trp Thr
225                 230                 235                 240 cag cag cag ctc gtg cag tat ttg cgc acc ggc agc gtg ccg ggc gtc        888
Gln Gln Gln Leu Val Gln Tyr Leu Arg Thr Gly Ser Val Pro Gly Val
                245                 250                 255 gcg cag gcg gcc ggg ccg atg gcc gag gcg gtc gag cac agc ttc tcg        936
Ala Gln Ala Ala Gly Pro Met Ala Glu Ala Val Glu His Ser Phe Ser
            260                 265                 270 aag atg acc gaa gcg gac atc ggt gcg atc gcc acg tac gtc cgc acg        984
Lys Met Thr Glu Ala Asp Ile Gly Ala Ile Ala Thr Tyr Val Arg Thr
        275                 280                 285 gtg ccg gcc gtt gcc gac agc aac gcg aag cag ccg cgg tcg tcg tgg       1032
Val Pro Ala Val Ala Asp Ser Asn Ala Lys Gln Pro Arg Ser Ser Trp
    290                 295                 300 ggc aag ccg gcc gag gac ggg ctg aag ctg cgc ggt gtc gcg ctc gcg       1080
```

-continued

```
Gly Lys Pro Ala Glu Asp Gly Leu Lys Leu Arg Gly Val Ala Leu Ala
305                 310                 315                 320 tcg tcg ggc atc gat ccg gcg cgg ctg tat ctc ggc aac tgc gcg acg      1128
Ser Ser Gly Ile Asp Pro Ala Arg Leu Tyr Leu Gly Asn Cys Ala Thr
                    325                 330                 335 tgc cac cag atg cag ggc aag ggc acg ccg gac ggt tac tac ccg tcg      1176
Cys His Gln Met Gln Gly Lys Gly Thr Pro Asp Gly Tyr Tyr Pro Ser
                340                 345                 350 ctg ttc cac aac tcc acc gtc ggc gcg tcg aat ccg tcg aac ctc gtg      1224
Leu Phe His Asn Ser Thr Val Gly Ala Ser Asn Pro Ser Asn Leu Val
            355                 360                 365 cag gtg atc ctg aac ggc gtg cag cgc aag atc ggc agc gag gat atc      1272
Gln Val Ile Leu Asn Gly Val Gln Arg Lys Ile Gly Ser Glu Asp Ile
        370                 375                 380 ggg atg ccc gct ttc cgc tac gat ctg aac gac gcg cag atc gcc gcg      1320
Gly Met Pro Ala Phe Arg Tyr Asp Leu Asn Asp Ala Gln Ile Ala Ala
385                 390                 395                 400 ctg acg aac tac gtg acc gcg cag ttc ggc aat ccg gcg gcg aag gtg      1368
Leu Thr Asn Tyr Val Thr Ala Gln Phe Gly Asn Pro Ala Ala Lys Val
                    405                 410                 415 acg gag cag gac gtc gcg aag ctg cgc tga catagtcggg cgcgccgaca        1418
Thr Glu Gln Asp Val Ala Lys Leu Arg
                420                 425 cggcgcaacc gataggacag gag                                            1441

<210> SEQ ID NO 6
<211> LENGTH: 425
<212> TYPE: PRT
<213> ORGANISM: Burkholderia cepacia

<400> SEQUENCE: 6

Val Arg Lys Ser Thr Leu Thr Phe Leu Ile Ala Gly Cys Leu Ala Leu
 1               5                  10                  15

Pro Gly Phe Ala Arg Ala Ala Asp Ala Ala Asp Pro Ala Leu Val Lys
                20                  25                  30

Arg Gly Glu Tyr Leu Ala Thr Ala Met Pro Val Pro Met Leu Gly Lys
            35                  40                  45

Ile Tyr Thr Ser Asn Ile Thr Pro Asp Pro Thr Gly Asp Cys Met
        50                  55                  60

Ala Cys His Thr Val Lys Gly Gly Lys Pro Tyr Ala Gly Gly Leu Gly
65                  70                  75                  80

Gly Ile Gly Lys Trp Thr Phe Glu Asp Phe Glu Arg Ala Val Arg His
                85                  90                  95

Gly Val Ser Lys Asn Gly Asp Asn Leu Tyr Pro Ala Met Pro Tyr Val
            100                 105                 110

Ser Tyr Ala Lys Ile Lys Asp Asp Val Arg Ala Leu Tyr Ala Tyr
        115                 120                 125

Phe Met His Gly Val Glu Pro Val Lys Gln Ala Pro Lys Asn Glu
    130                 135                 140

Ile Pro Ala Leu Leu Ser Met Arg Trp Pro Leu Lys Ile Trp Asn Trp
145                 150                 155                 160

Leu Phe Leu Lys Asp Gly Pro Tyr Gln Pro Lys Pro Ser Gln Ser Ala
                165                 170                 175

Glu Trp Asn Arg Gly Ala Tyr Leu Val Gln Gly Leu Ala His Cys Ser
            180                 185                 190

Thr Cys His Thr Pro Arg Gly Ile Ala Met Gln Glu Lys Ser Leu Asp
        195                 200                 205
```

Glu Thr Gly Gly Ser Phe Leu Ala Gly Ser Val Leu Ala Gly Trp Asp
    210                 215                 220

Gly Tyr Asn Ile Thr Ser Asp Pro Asn Ala Gly Ile Gly Ser Trp Thr
225                 230                 235                 240

Gln Gln Gln Leu Val Gln Tyr Leu Arg Thr Gly Ser Val Pro Gly Val
                245                 250                 255

Ala Gln Ala Ala Gly Pro Met Ala Glu Ala Val Glu His Ser Phe Ser
            260                 265                 270

Lys Met Thr Glu Ala Asp Ile Gly Ala Ile Ala Thr Tyr Val Arg Thr
        275                 280                 285

Val Pro Ala Val Ala Asp Ser Asn Ala Lys Gln Pro Arg Ser Ser Trp
    290                 295                 300

Gly Lys Pro Ala Glu Asp Gly Leu Lys Leu Arg Gly Val Ala Leu Ala
305                 310                 315                 320

Ser Ser Gly Ile Asp Pro Ala Arg Leu Tyr Leu Gly Asn Cys Ala Thr
                325                 330                 335

Cys His Gln Met Gln Gly Lys Gly Thr Pro Asp Gly Tyr Tyr Pro Ser
            340                 345                 350

Leu Phe His Asn Ser Thr Val Gly Ala Ser Asn Pro Ser Asn Leu Val
        355                 360                 365

Gln Val Ile Leu Asn Gly Val Gln Arg Lys Ile Gly Ser Glu Asp Ile
    370                 375                 380

Gly Met Pro Ala Phe Arg Tyr Asp Leu Asn Asp Ala Gln Ile Ala Ala
385                 390                 395                 400

Leu Thr Asn Tyr Val Thr Ala Gln Phe Gly Asn Pro Ala Ala Lys Val
                405                 410                 415

Thr Glu Gln Asp Val Ala Lys Leu Arg
            420                 425

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide
<221> NAME/KEY: misc_feature
<222> LOCATION: (6)..(6)
<223> OTHER INFORMATION: Xaa can be any naturally occurring amino acid
      other than serine

<400> SEQUENCE: 7

Lys Lys Ile His Leu Xaa Asn
  1               5

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 8
catgccatgg cacacaacga caacac                                          26

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
gtcgacgatc ttcttccagc cgaacatcac                                30

<210> SEQ ID NO 10
<211> LENGTH: 41
<212> TYPE: DNA
<213> ORGANISM: Artificial Sequence
<220> FEATURE:
<223> OTHER INFORMATION: primer

<400> SEQUENCE: 10
ggaaatcgtc gagcgcttct ttaatcagcc cgacaagatg g                    41

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
cgagcgcttc cgctttcagc ccgacaagat g                               31

<210> SEQ ID NO 12
<211> LENGTH: 39
<212> TYPE: DNA
<213> ORGANISM: Artificial Sequence
<220> FEATURE:
<223> OTHER INFORMATION: primer

<400> SEQUENCE: 12
gtcgagcgct tccgcaattt tcccgacaag atggacttc                       39

<210> SEQ ID NO 13
<211> LENGTH: 41
<212> TYPE: DNA
<213> ORGANISM: Artificial Sequence
<220> FEATURE:
<223> OTHER INFORMATION: primer

<400> SEQUENCE: 13
gagcgcttcc gcaatcagtt tgacaagatg gacttcatgg c                    41

<210> SEQ ID NO 14
<211> LENGTH: 39
<212> TYPE: DNA
<213> ORGANISM: Artificial Sequence
<220> FEATURE:
<223> OTHER INFORMATION: primer

<400> SEQUENCE: 14
gcttccgcaa tcagcccttt aagatggact tcatggcgc                       39

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15
ccgcaatcag cccgacttta tggacttcat ggcgccg                         37

<210> SEQ ID NO 16

```
<211> LENGTH: 35
<212> TYPE: DNA
<213> ORGANISM: Artificial Sequence
<220> FEATURE:
<223> OTHER INFORMATION: primer

<400> SEQUENCE: 16
gcaatcagcc cgacaagttt gacttcatgg cgccg                              35

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
caatcagccc gacaagatgt ttttcatggc gccgtaccc                           39

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
cgacaagatg gacttctttg cgccgtaccc gtc                                33

<210> SEQ ID NO 19
<211> LENGTH: 39
<212> TYPE: DNA
<213> ORGANISM: Artificial Sequence
<220> FEATURE:
<223> OTHER INFORMATION: primer

<400> SEQUENCE: 19
cgacaagatg gacttcatgt ttccgtaccc gtcgagccc                           39

<210> SEQ ID NO 20
<211> LENGTH: 39
<212> TYPE: DNA
<213> ORGANISM: Artificial Sequence
<220> FEATURE:
<223> OTHER INFORMATION: primer

<400> SEQUENCE: 20
caagatggac ttcatggcgt tttacccgtc gagccctg                            39

<210> SEQ ID NO 21
<211> LENGTH: 29
<212> TYPE: DNA
<213> ORGANISM: Artificial Sequence
<220> FEATURE:
<223> OTHER INFORMATION: primer

<400> SEQUENCE: 21
acttcatggc gccgtttccg tcgagcccc                                     29

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
```
cttcatggcg ccgtactttt cgagcccctg ggc                           33

<210> SEQ ID NO 23
<211> LENGTH: 27
<212> TYPE: DNA
<213> ORGANISM: Artificial Sequence
<220> FEATURE:
<223> OTHER INFORMATION: primer

<400> SEQUENCE: 23
gcgccgtacc cgtttagccc ctgggcg                                  27

<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24
cgccgtaccc gtcgtttccc tgggcgccg                                29

<210> SEQ ID NO 25
<211> LENGTH: 33
<212> TYPE: DNA
<213> ORGANISM: Artificial Sequence
<220> FEATURE:
<223> OTHER INFORMATION: primer

<400> SEQUENCE: 25
ccgtacccgt cgagcttttg ggcgccgcat ccc                           33

<210> SEQ ID NO 26
<211> LENGTH: 27
<212> TYPE: DNA
<213> ORGANISM: Artificial Sequence
<220> FEATURE:
<223> OTHER INFORMATION: primer

<400> SEQUENCE: 26
ccgtcgagcc cctttgcgcc gcatccc                                  27

<210> SEQ ID NO 27
<211> LENGTH: 33
<212> TYPE: DNA
<213> ORGANISM: Artificial Sequence
<220> FEATURE:
<223> OTHER INFORMATION: primer

<400> SEQUENCE: 27
cgtcgagccc ctggtttccg catcccgagt acg                           33

<210> SEQ ID NO 28
<211> LENGTH: 33
<212> TYPE: DNA
<213> ORGANISM: Artificial Sequence
<220> FEATURE:
<223> OTHER INFORMATION: primer

<400> SEQUENCE: 28
cgagcccctg ggcgtttcat cccgagtacg gcc                           33

<210> SEQ ID NO 29
<211> LENGTH: 27
<212> TYPE: DNA

<210> SEQ ID NO 30
<211> LENGTH: 43
<212> TYPE: DNA
<213> ORGANISM: Artificial Sequence
<220> FEATURE:
<223> OTHER INFORMATION: primer

<400> SEQUENCE: 29
ccctgggcgc cgtttcccga gtacggc         27

<210> SEQ ID NO 30
<211> LENGTH: 43
<212> TYPE: DNA
<213> ORGANISM: Artificial Sequence
<220> FEATURE:
<223> OTHER INFORMATION: primer

<400> SEQUENCE: 30
ctacctgatc ctgaagggct ttcacaagtt caactcgcag tac         43

<210> SEQ ID NO 31
<211> LENGTH: 43
<212> TYPE: DNA
<213> ORGANISM: Artificial Sequence
<220> FEATURE:
<223> OTHER INFORMATION: primer

<400> SEQUENCE: 31
cctgatcctg aagggcgagt ttaagttcaa ctcgcagtac atc         43

<210> SEQ ID NO 32
<211> LENGTH: 41
<212> TYPE: DNA
<213> ORGANISM: Artificial Sequence
<220> FEATURE:
<223> OTHER INFORMATION: primer

<400> SEQUENCE: 32
atcctgaagg gcgagcactt tttcaactcg cagtacatcc g         41

<210> SEQ ID NO 33
<211> LENGTH: 37
<212> TYPE: DNA
<213> ORGANISM: Artificial Sequence
<220> FEATURE:
<223> OTHER INFORMATION: primer

<400> SEQUENCE: 33
agggcgagca caagttcttt tcgcagtaca tccgcgc         37

<210> SEQ ID NO 34
<211> LENGTH: 35
<212> TYPE: DNA
<213> ORGANISM: Artificial Sequence
<220> FEATURE:
<223> OTHER INFORMATION: primer

<400> SEQUENCE: 34
gcgagcacaa gttcaacttt cagtacatcc gcgcg         35

<210> SEQ ID NO 35
<211> LENGTH: 39
<212> TYPE: DNA
<213> ORGANISM: Artificial Sequence
<220> FEATURE:
<223> OTHER INFORMATION: primer

<400> SEQUENCE: 35
cgagcacaag ttcaactcgt tttacatccg cgcggtggg         39

<210> SEQ ID NO 36
<211> LENGTH: 33
<212> TYPE: DNA
<213> ORGANISM: Artificial Sequence
<220> FEATURE:
<223> OTHER INFORMATION: primer

<400> SEQUENCE: 36
caagttcaac tcgcagttta tccgcgcggt ggg                        33

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37
gttcaactcg cagtactttc gcgcggtggg c                          31

<210> SEQ ID NO 38
<211> LENGTH: 37
<212> TYPE: DNA
<213> ORGANISM: Artificial Sequence
<220> FEATURE:
<223> OTHER INFORMATION: primer

<400> SEQUENCE: 38
gttcaactcg cagtacatct ttgcggtggg cggcacg                    37

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39
ctcgcagtac atccgctttg tgggcggcac gac                        33

<210> SEQ ID NO 40
<211> LENGTH: 29
<212> TYPE: DNA
<213> ORGANISM: Artificial Sequence
<220> FEATURE:
<223> OTHER INFORMATION: primer

<400> SEQUENCE: 40
agtacatccg cgcgtttggc ggcacgacg                             29

<210> SEQ ID NO 41
<211> LENGTH: 33
<212> TYPE: DNA
<213> ORGANISM: Artificial Sequence
<220> FEATURE:
<223> OTHER INFORMATION: primer

<400> SEQUENCE: 41
tacatccgcg cggtgtttgg cacgacgtgg cac                        33

<210> SEQ ID NO 42
<211> LENGTH: 31
<212> TYPE: DNA
<213> ORGANISM: Artificial Sequence
<220> FEATURE:

-continued

<223> OTHER INFORMATION: primer

<400> SEQUENCE: 42
ccgcgcggtg ggctttacga cgtggcactg g                                31

<210> SEQ ID NO 43
<211> LENGTH: 31
<212> TYPE: DNA
<213> ORGANISM: Artificial Sequence
<220> FEATURE:
<223> OTHER INFORMATION: primer

<400> SEQUENCE: 43
cgcggtgggc ggctttacgt ggcactgggc c                                31

<210> SEQ ID NO 44
<211> LENGTH: 31
<212> TYPE: DNA
<213> ORGANISM: Artificial Sequence
<220> FEATURE:
<223> OTHER INFORMATION: primer

<400> SEQUENCE: 44
cggtgggcgg cacgttttgg cactgggccg c                                31

<210> SEQ ID NO 45
<211> LENGTH: 27
<212> TYPE: DNA
<213> ORGANISM: Artificial Sequence
<220> FEATURE:
<223> OTHER INFORMATION: primer

<400> SEQUENCE: 45
ggcggcacga cgtttcactg ggccgcg                                     27

<210> SEQ ID NO 46
<211> LENGTH: 31
<212> TYPE: DNA
<213> ORGANISM: Artificial Sequence
<220> FEATURE:
<223> OTHER INFORMATION: primer

<400> SEQUENCE: 46
gcggcacgac gtggttttgg gccgcgtcgg c                                31

<210> SEQ ID NO 47
<211> LENGTH: 29
<212> TYPE: DNA
<213> ORGANISM: Artificial Sequence
<220> FEATURE:
<223> OTHER INFORMATION: primer

<400> SEQUENCE: 47
gcacgacgtg gcactttgcc gcgtcggcg                                   29

<210> SEQ ID NO 48
<211> LENGTH: 31
<212> TYPE: DNA
<213> ORGANISM: Artificial Sequence
<220> FEATURE:
<223> OTHER INFORMATION: primer

<400> SEQUENCE: 48
cgacgtggca ctggtttgcg tcggcgtggc g                                31

<210> SEQ ID NO 49
<211> LENGTH: 33
<212> TYPE: DNA
<213> ORGANISM: Artificial Sequence
<220> FEATURE:
<223> OTHER INFORMATION: primer

<400> SEQUENCE: 49
acgtggcact gggccttttc ggcgtggcgc ttc                           33

<210> SEQ ID NO 50
<211> LENGTH: 35
<212> TYPE: DNA
<213> ORGANISM: Artificial Sequence
<220> FEATURE:
<223> OTHER INFORMATION: primer

<400> SEQUENCE: 50
cccgaacggt gtcgcgttta gctcggacat ggtcg                         35

<210> SEQ ID NO 51
<211> LENGTH: 35
<212> TYPE: DNA
<213> ORGANISM: Artificial Sequence
<220> FEATURE:
<223> OTHER INFORMATION: primer

<400> SEQUENCE: 51
gaacggtgtc gcgaactttt cggacatggt cggcc                         35

<210> SEQ ID NO 52
<211> LENGTH: 31
<212> TYPE: DNA
<213> ORGANISM: Artificial Sequence
<220> FEATURE:
<223> OTHER INFORMATION: primer

<400> SEQUENCE: 52
gtgtcgcgaa cagctttgac atggtcggcc g                             31

<210> SEQ ID NO 53
<211> LENGTH: 35
<212> TYPE: DNA
<213> ORGANISM: Artificial Sequence
<220> FEATURE:
<223> OTHER INFORMATION: primer

<400> SEQUENCE: 53
tgtcgcgaac agctcgttta tggtcggccg caacc                         35

<210> SEQ ID NO 54
<211> LENGTH: 31
<212> TYPE: DNA
<213> ORGANISM: Artificial Sequence
<220> FEATURE:
<223> OTHER INFORMATION: primer

<400> SEQUENCE: 54
cgaacagctc ggactttgtc ggccgcaacc t                             31

<210> SEQ ID NO 55
<211> LENGTH: 35
<212> TYPE: DNA
<213> ORGANISM: Artificial Sequence
<220> FEATURE:
<223> OTHER INFORMATION: primer

<400> SEQUENCE: 55
cgaacagctc ggacatgttt ggccgcaacc tgatg                          35

<210> SEQ ID NO 56
<211> LENGTH: 41
<212> TYPE: DNA
<213> ORGANISM: Artificial Sequence
<220> FEATURE:
<223> OTHER INFORMATION: primer

<400> SEQUENCE: 56
gaacagctcg gacatggtct ttcgcaacct gatggaccat c                   41

<210> SEQ ID NO 57
<211> LENGTH: 37
<212> TYPE: DNA
<213> ORGANISM: Artificial Sequence
<220> FEATURE:
<223> OTHER INFORMATION: primer

<400> SEQUENCE: 57
ctcggacatg gtcggcttta acctgatgga ccatccg                        37

<210> SEQ ID NO 58
<211> LENGTH: 35
<212> TYPE: DNA
<213> ORGANISM: Artificial Sequence
<220> FEATURE:
<223> OTHER INFORMATION: primer

<400> SEQUENCE: 58
ggacatggtc ggccgctttc tgatggacca tccgg                          35

<210> SEQ ID NO 59
<211> LENGTH: 31
<212> TYPE: DNA
<213> ORGANISM: Artificial Sequence
<220> FEATURE:
<223> OTHER INFORMATION: primer

<400> SEQUENCE: 59
ggtcggccgc aactttatgg accatccggg c                              31

<210> SEQ ID NO 60
<211> LENGTH: 29
<212> TYPE: DNA
<213> ORGANISM: Artificial Sequence
<220> FEATURE:
<223> OTHER INFORMATION: primer

<400> SEQUENCE: 60
cggccgcaac ctgtttgacc atccgggca                                 29

<210> SEQ ID NO 61
<211> LENGTH: 33
<212> TYPE: DNA
<213> ORGANISM: Artificial Sequence
<220> FEATURE:
<223> OTHER INFORMATION: primer

<400> SEQUENCE: 61
cggccgcaac ctgatgtttc atccgggcac cgg                            33

<210> SEQ ID NO 62
<211> LENGTH: 29

<212> TYPE: DNA
<213> ORGANISM: Artificial Sequence
<220> FEATURE:
<223> OTHER INFORMATION: primer

<400> SEQUENCE: 62
gcaacctgat ggactttccg ggcaccggc                                29

<210> SEQ ID NO 63
<211> LENGTH: 35
<212> TYPE: DNA
<213> ORGANISM: Artificial Sequence
<220> FEATURE:
<223> OTHER INFORMATION: primer

<400> SEQUENCE: 63
gcaacctgat ggaccatttt ggcaccggcg tgtcg                         35

<210> SEQ ID NO 64
<211> LENGTH: 41
<212> TYPE: DNA
<213> ORGANISM: Artificial Sequence
<220> FEATURE:
<223> OTHER INFORMATION: primer

<400> SEQUENCE: 64
caacctgatg gaccatccgt ttaccggcgt gtcgttctat g                  41

<210> SEQ ID NO 65
<211> LENGTH: 37
<212> TYPE: DNA
<213> ORGANISM: Artificial Sequence
<220> FEATURE:
<223> OTHER INFORMATION: primer

<400> SEQUENCE: 65
tgatggacca tccgggcttt ggcgtgtcgt tctatgc                       37

<210> SEQ ID NO 66
<211> LENGTH: 37
<212> TYPE: DNA
<213> ORGANISM: Artificial Sequence
<220> FEATURE:
<223> OTHER INFORMATION: primer

<400> SEQUENCE: 66
ggaccatccg ggcacctttg tgtcgttcta tgcgagc                       37

<210> SEQ ID NO 67
<211> LENGTH: 31
<212> TYPE: DNA
<213> ORGANISM: Artificial Sequence
<220> FEATURE:
<223> OTHER INFORMATION: primer

<400> SEQUENCE: 67
tccgggcacc ggcttttcgt tctatgcgag c                             31

<210> SEQ ID NO 68
<211> LENGTH: 31
<212> TYPE: DNA
<213> ORGANISM: Artificial Sequence
<220> FEATURE:
<223> OTHER INFORMATION: primer

<400> SEQUENCE: 68
gggcaccggc gtgtttttct atgcgagcga g                                      31

<210> SEQ ID NO 69
<211> LENGTH: 29
<212> TYPE: DNA
<213> ORGANISM: Artificial Sequence
<220> FEATURE:
<223> OTHER INFORMATION: primer

<400> SEQUENCE: 69
cggcgtgtcg ttctttgcga gcgagaagc                                         29

<210> SEQ ID NO 70
<211> LENGTH: 37
<212> TYPE: DNA
<213> ORGANISM: Artificial Sequence
<220> FEATURE:
<223> OTHER INFORMATION: primer

<400> SEQUENCE: 70
ccggcgtgtc gttctatttt agcgagaagc tgtggcc                                37

<210> SEQ ID NO 71
<211> LENGTH: 37
<212> TYPE: DNA
<213> ORGANISM: Artificial Sequence
<220> FEATURE:
<223> OTHER INFORMATION: primer

<400> SEQUENCE: 71
ggcgtgtcgt tctatgcgtt tgagaagctg tggccgg                                37

<210> SEQ ID NO 72
<211> LENGTH: 37
<212> TYPE: DNA
<213> ORGANISM: Artificial Sequence
<220> FEATURE:
<223> OTHER INFORMATION: primer

<400> SEQUENCE: 72
gtgtcgttct atgcgagctt taagctgtgg ccgggcc                                37

<210> SEQ ID NO 73
<211> LENGTH: 33
<212> TYPE: DNA
<213> ORGANISM: Artificial Sequence
<220> FEATURE:
<223> OTHER INFORMATION: primer

<400> SEQUENCE: 73
gttctatgcg agcgagtttc tgtggccggg ccg                                    33

<210> SEQ ID NO 74
<211> LENGTH: 29
<212> TYPE: DNA
<213> ORGANISM: Artificial Sequence
<220> FEATURE:
<223> OTHER INFORMATION: primer

<400> SEQUENCE: 74
atgcgagcga gaagttttgg ccgggccgc                                         29

<210> SEQ ID NO 75
<211> LENGTH: 29
<212> TYPE: DNA
<213> ORGANISM: Artificial Sequence

```
<220> FEATURE:
<223> OTHER INFORMATION: primer

<400> SEQUENCE: 75
cgagcgagaa gctgtttccg ggccgcggc                                    29

<210> SEQ ID NO 76
<211> LENGTH: 31
<212> TYPE: DNA
<213> ORGANISM: Artificial Sequence
<220> FEATURE:
<223> OTHER INFORMATION: primer

<400> SEQUENCE: 76
agcgagaagc tgtggtttgg ccgcggcccg c                                 31

<210> SEQ ID NO 77
<211> LENGTH: 31
<212> TYPE: DNA
<213> ORGANISM: Artificial Sequence
<220> FEATURE:
<223> OTHER INFORMATION: primer

<400> SEQUENCE: 77
gagaagctgt ggccgtttcg cggcccgcag g                                 31

<210> SEQ ID NO 78
<211> LENGTH: 35
<212> TYPE: DNA
<213> ORGANISM: Artificial Sequence
<220> FEATURE:
<223> OTHER INFORMATION: primer

<400> SEQUENCE: 78
cgaagcggcg aagaagtttc acctgtcgaa cctgt                             35

<210> SEQ ID NO 79
<211> LENGTH: 39
<212> TYPE: DNA
<213> ORGANISM: Artificial Sequence
<220> FEATURE:
<223> OTHER INFORMATION: primer

<400> SEQUENCE: 79
cgaagcggcg aagaagatct ttctgtcgaa cctgtcgcg                         39

<210> SEQ ID NO 80
<211> LENGTH: 35
<212> TYPE: DNA
<213> ORGANISM: Artificial Sequence
<220> FEATURE:
<223> OTHER INFORMATION: primer

<400> SEQUENCE: 80
ggcgaagaag atccactttt cgaacctgtc gcgca                             35

<210> SEQ ID NO 81
<211> LENGTH: 37
<212> TYPE: DNA
<213> ORGANISM: Artificial Sequence
<220> FEATURE:
<223> OTHER INFORMATION: primer

<400> SEQUENCE: 81
gcgaagaaga tccacctgtt taacctgtcg cgcatcg                           37
```

<210> SEQ ID NO 82
<211> LENGTH: 39
<212> TYPE: DNA
<213> ORGANISM: Artificial Sequence
<220> FEATURE:
<223> OTHER INFORMATION: primer

<400> SEQUENCE: 82
gaagaagatc cacctgtcgt ttctgtcgcg catcgacca                        39

<210> SEQ ID NO 83
<211> LENGTH: 35
<212> TYPE: DNA
<213> ORGANISM: Artificial Sequence
<220> FEATURE:
<223> OTHER INFORMATION: primer

<400> SEQUENCE: 83
agatccacct gtcgaacttt tcgcgcatcg accag                            35

<210> SEQ ID NO 84
<211> LENGTH: 33
<212> TYPE: DNA
<213> ORGANISM: Artificial Sequence
<220> FEATURE:
<223> OTHER INFORMATION: primer

<400> SEQUENCE: 84
cacctgtcga acctgtttcg catcgaccag gag                              33

<210> SEQ ID NO 85
<211> LENGTH: 39
<212> TYPE: DNA
<213> ORGANISM: Artificial Sequence
<220> FEATURE:
<223> OTHER INFORMATION: primer

<400> SEQUENCE: 85
cacctgtcga acctgtcgtt tatcgaccag gagacgcag                        39

<210> SEQ ID NO 86
<211> LENGTH: 31
<212> TYPE: DNA
<213> ORGANISM: Artificial Sequence
<220> FEATURE:
<223> OTHER INFORMATION: primer

<400> SEQUENCE: 86
cgaacctgtc gcgctttgac caggagacgc a                                31

<210> SEQ ID NO 87
<211> LENGTH: 39
<212> TYPE: DNA
<213> ORGANISM: Artificial Sequence
<220> FEATURE:
<223> OTHER INFORMATION: primer

<400> SEQUENCE: 87
cgaacctgtc gcgcatcttt caggagacgc agaagatct                        39

<210> SEQ ID NO 88
<211> LENGTH: 43
<212> TYPE: DNA
<213> ORGANISM: Artificial Sequence
<220> FEATURE:
<223> OTHER INFORMATION: primer

<400> SEQUENCE: 88
gaacctgtcg cgcatcgact ttgagacgca gaagatcttc aag    43

<210> SEQ ID NO 89
<211> LENGTH: 41
<212> TYPE: DNA
<213> ORGANISM: Artificial Sequence
<220> FEATURE:
<223> OTHER INFORMATION: primer

<400> SEQUENCE: 89
ctgtcgcgca tcgaccagtt tacgcagaag atcttcaagg c    41

<210> SEQ ID NO 90
<211> LENGTH: 39
<212> TYPE: DNA
<213> ORGANISM: Artificial Sequence
<220> FEATURE:
<223> OTHER INFORMATION: primer

<400> SEQUENCE: 90
cgcgcatcga ccaggagttt cagaagatct tcaaggccg    39

<210> SEQ ID NO 91
<211> LENGTH: 39
<212> TYPE: DNA
<213> ORGANISM: Artificial Sequence
<220> FEATURE:
<223> OTHER INFORMATION: primer

<400> SEQUENCE: 91
gcatcgacca ggagacgttt aagatcttca aggccggca    39

<210> SEQ ID NO 92
<211> LENGTH: 37
<212> TYPE: DNA
<213> ORGANISM: Artificial Sequence
<220> FEATURE:
<223> OTHER INFORMATION: primer

<400> SEQUENCE: 92
cgaccaggag acgcagttta tcttcaaggc cggcaag    37

<210> SEQ ID NO 93
<211> LENGTH: 35
<212> TYPE: DNA
<213> ORGANISM: Artificial Sequence
<220> FEATURE:
<223> OTHER INFORMATION: primer

<400> SEQUENCE: 93
ccaggagacg cagaagtttt tcaaggccgg caagc    35

<210> SEQ ID NO 94
<211> LENGTH: 33
<212> TYPE: DNA
<213> ORGANISM: Artificial Sequence
<220> FEATURE:
<223> OTHER INFORMATION: primer

<400> SEQUENCE: 94
cccgacgagc tcgactttca gatccgcgac cgt    33

<210> SEQ ID NO 95

<211> LENGTH: 33
<212> TYPE: DNA
<213> ORGANISM: Artificial Sequence
<220> FEATURE:
<223> OTHER INFORMATION: primer

<400> SEQUENCE: 95
gacgagctcg acgcgtttat ccgcgaccgt tcc                          33

<210> SEQ ID NO 96
<211> LENGTH: 29
<212> TYPE: DNA
<213> ORGANISM: Artificial Sequence
<220> FEATURE:
<223> OTHER INFORMATION: primer

<400> SEQUENCE: 96
gctcgacgcg cagtttcgcg accgttccg                              29

<210> SEQ ID NO 97
<211> LENGTH: 33
<212> TYPE: DNA
<213> ORGANISM: Artificial Sequence
<220> FEATURE:
<223> OTHER INFORMATION: primer

<400> SEQUENCE: 97
ctcgacgcgc agatctttga ccgttccgca cgc                          33

<210> SEQ ID NO 98
<211> LENGTH: 33
<212> TYPE: DNA
<213> ORGANISM: Artificial Sequence
<220> FEATURE:
<223> OTHER INFORMATION: primer

<400> SEQUENCE: 98
gacgcgcaga tccgctttcg ttccgcacgc tac                          33

<210> SEQ ID NO 99
<211> LENGTH: 31
<212> TYPE: DNA
<213> ORGANISM: Artificial Sequence
<220> FEATURE:
<223> OTHER INFORMATION: primer

<400> SEQUENCE: 99
cgcagatccg cgactttcc gcacgctacg t                            31

<210> SEQ ID NO 100
<211> LENGTH: 33
<212> TYPE: DNA
<213> ORGANISM: Artificial Sequence
<220> FEATURE:
<223> OTHER INFORMATION: primer

<400> SEQUENCE: 100
cagatccgcg accgttttgc acgctacgtg cag                          33

<210> SEQ ID NO 101
<211> LENGTH: 35
<212> TYPE: DNA
<213> ORGANISM: Artificial Sequence
<220> FEATURE:
<223> OTHER INFORMATION: primer

<400> SEQUENCE: 101

```
gatccgcgac cgttcctttc gctacgtgca gttcg                              35

<210> SEQ ID NO 102
<211> LENGTH: 37
<212> TYPE: DNA
<213> ORGANISM: Artificial Sequence
<220> FEATURE:
<223> OTHER INFORMATION: primer

<400> SEQUENCE: 102
ccgcgaccgt tccgcatttt acgtgcagtt cgactgc                            37

<210> SEQ ID NO 103
<211> LENGTH: 31
<212> TYPE: DNA
<213> ORGANISM: Artificial Sequence
<220> FEATURE:
<223> OTHER INFORMATION: primer

<400> SEQUENCE: 103
ccgttccgca cgctttgtgc agttcgactg c                                  31

<210> SEQ ID NO 104
<211> LENGTH: 35
<212> TYPE: DNA
<213> ORGANISM: Artificial Sequence
<220> FEATURE:
<223> OTHER INFORMATION: primer

<400> SEQUENCE: 104
ccgttccgca cgctactttc agttcgactg cttcc                              35

<210> SEQ ID NO 105
<211> LENGTH: 41
<212> TYPE: DNA
<213> ORGANISM: Artificial Sequence
<220> FEATURE:
<223> OTHER INFORMATION: primer

<400> SEQUENCE: 105
cgttccgcac gctacgtgtt tttcgactgc ttccacgaaa t                       41

<210> SEQ ID NO 106
<211> LENGTH: 41
<212> TYPE: DNA
<213> ORGANISM: Artificial Sequence
<220> FEATURE:
<223> OTHER INFORMATION: primer

<400> SEQUENCE: 106
cgcacgctac gtgcagttct tttgcttcca cgaaatcctg c                       41

<210> SEQ ID NO 107
<211> LENGTH: 37
<212> TYPE: DNA
<213> ORGANISM: Artificial Sequence
<220> FEATURE:
<223> OTHER INFORMATION: primer

<400> SEQUENCE: 107
gctacgtgca gttcgacttt ttccacgaaa tcctgcc                            37

<210> SEQ ID NO 108
<211> LENGTH: 39
<212> TYPE: DNA
```

<213> ORGANISM: Artificial Sequence
<220> FEATURE:
<223> OTHER INFORMATION: primer

<400> SEQUENCE: 108
gtgcagttcg actgcttctt tgaaatcctg ccgcaaccc                                39

<210> SEQ ID NO 109
<211> LENGTH: 37
<212> TYPE: DNA
<213> ORGANISM: Artificial Sequence
<220> FEATURE:
<223> OTHER INFORMATION: primer

<400> SEQUENCE: 109
cagttcgact gcttccactt tatcctgccg caacccg                                  37

<210> SEQ ID NO 110
<211> LENGTH: 33
<212> TYPE: DNA
<213> ORGANISM: Artificial Sequence
<220> FEATURE:
<223> OTHER INFORMATION: primer

<400> SEQUENCE: 110
cgactgcttc cacgaatttc tgccgcaacc cga                                      33

<210> SEQ ID NO 111
<211> LENGTH: 37
<212> TYPE: DNA
<213> ORGANISM: Artificial Sequence
<220> FEATURE:
<223> OTHER INFORMATION: primer

<400> SEQUENCE: 111
gactgcttcc acgaaatctt tccgcaaccc gagaacc                                  37

<210> SEQ ID NO 112
<211> LENGTH: 39
<212> TYPE: DNA
<213> ORGANISM: Artificial Sequence
<220> FEATURE:
<223> OTHER INFORMATION: primer

<400> SEQUENCE: 112
ccacgaaatc ctgccgcaat ttgagaaccg catcgtgcc                                39

<210> SEQ ID NO 113
<211> LENGTH: 37
<212> TYPE: DNA
<213> ORGANISM: Artificial Sequence
<220> FEATURE:
<223> OTHER INFORMATION: primer

<400> SEQUENCE: 113
aaatcctgcc gcaacccttt aaccgcatcg tgccgag                                  37

<210> SEQ ID NO 114
<211> LENGTH: 33
<212> TYPE: DNA
<213> ORGANISM: Artificial Sequence
<220> FEATURE:
<223> OTHER INFORMATION: primer

<400> SEQUENCE: 114
ctgccgcaac ccgagtttcg catcgtgccg agc                                      33

<210> SEQ ID NO 115
<211> LENGTH: 37
<212> TYPE: DNA
<213> ORGANISM: Artificial Sequence
<220> FEATURE:
<223> OTHER INFORMATION: primer

<400> SEQUENCE: 115
gccgcaaccc gagaacttta tcgtgccgag caagacg         37

<210> SEQ ID NO 116
<211> LENGTH: 33
<212> TYPE: DNA
<213> ORGANISM: Artificial Sequence
<220> FEATURE:
<223> OTHER INFORMATION: primer

<400> SEQUENCE: 116
caacccgaga accgctttgt gccgagcaag acg         33

<210> SEQ ID NO 117
<211> LENGTH: 31
<212> TYPE: DNA
<213> ORGANISM: Artificial Sequence
<220> FEATURE:
<223> OTHER INFORMATION: primer

<400> SEQUENCE: 117
ccgagaaccg catctttccg agcaagacgg c         31

<210> SEQ ID NO 118
<211> LENGTH: 35
<212> TYPE: DNA
<213> ORGANISM: Artificial Sequence
<220> FEATURE:
<223> OTHER INFORMATION: primer

<400> SEQUENCE: 118
cgagaaccgc atcgtgttta gcaagacggc gaccg         35

<210> SEQ ID NO 119
<211> LENGTH: 35
<212> TYPE: DNA
<213> ORGANISM: Artificial Sequence
<220> FEATURE:
<223> OTHER INFORMATION: primer

<400> SEQUENCE: 119
gaaccgcatc gtgccgttta agacggcgac cgatg         35

<210> SEQ ID NO 120
<211> LENGTH: 33
<212> TYPE: DNA
<213> ORGANISM: Artificial Sequence
<220> FEATURE:
<223> OTHER INFORMATION: primer

<400> SEQUENCE: 120
cgcatcgtgc cgagctttac ggcgaccgat gcg         33

<210> SEQ ID NO 121
<211> LENGTH: 35
<212> TYPE: DNA
<213> ORGANISM: Artificial Sequence
<220> FEATURE:

<223> OTHER INFORMATION: primer

<400> SEQUENCE: 121
catcgtgccg agcaagtttg cgaccgatgc gatcg    35

<210> SEQ ID NO 122
<211> LENGTH: 35
<212> TYPE: DNA
<213> ORGANISM: Artificial Sequence
<220> FEATURE:
<223> OTHER INFORMATION: primer

<400> SEQUENCE: 122
cgtgccgagc aagacgttta ccgatgcgat cggca    35

<210> SEQ ID NO 123
<211> LENGTH: 35
<212> TYPE: DNA
<213> ORGANISM: Artificial Sequence
<220> FEATURE:
<223> OTHER INFORMATION: primer

<400> SEQUENCE: 123
ccgagcaaga cggcgttttga tgcgatcggc attcc    35

<210> SEQ ID NO 124
<211> LENGTH: 31
<212> TYPE: DNA
<213> ORGANISM: Artificial Sequence
<220> FEATURE:
<223> OTHER INFORMATION: primer

<400> SEQUENCE: 124
gcaagacggc gacctttgcg atcggcattc c    31

<210> SEQ ID NO 125
<211> LENGTH: 35
<212> TYPE: DNA
<213> ORGANISM: Artificial Sequence
<220> FEATURE:
<223> OTHER INFORMATION: primer

<400> SEQUENCE: 125
caagacggcg accgattttta tcggcattcc gcgcc    35

<210> SEQ ID NO 126
<211> LENGTH: 29
<212> TYPE: DNA
<213> ORGANISM: Artificial Sequence
<220> FEATURE:
<223> OTHER INFORMATION: primer

<400> SEQUENCE: 126
ggcgaccgat gcgtttggca ttccgcgcc    29

<210> SEQ ID NO 127
<211> LENGTH: 33
<212> TYPE: DNA
<213> ORGANISM: Artificial Sequence
<220> FEATURE:
<223> OTHER INFORMATION: primer

<400> SEQUENCE: 127
gcgaccgatg cgatctttat tccgcgcccc gag    33

<210> SEQ ID NO 128
<211> LENGTH: 23
<212> TYPE: DNA
<213> ORGANISM: Artificial Sequence
<220> FEATURE:
<223> OTHER INFORMATION: primer

<400> SEQUENCE: 128
tgcgatcggc tttccgcgcc ccg                                           23

<210> SEQ ID NO 129
<211> LENGTH: 35
<212> TYPE: DNA
<213> ORGANISM: Artificial Sequence
<220> FEATURE:
<223> OTHER INFORMATION: primer

<400> SEQUENCE: 129
ccgatgcgat cggcattttt cgccccgaga tcacg                              35

<210> SEQ ID NO 130
<211> LENGTH: 39
<212> TYPE: DNA
<213> ORGANISM: Artificial Sequence
<220> FEATURE:
<223> OTHER INFORMATION: primer

<400> SEQUENCE: 130
gatgcgatcg gcattccgtt tcccgagatc acgtatgcg                          39

<210> SEQ ID NO 131
<211> LENGTH: 39
<212> TYPE: DNA
<213> ORGANISM: Artificial Sequence
<220> FEATURE:
<223> OTHER INFORMATION: primer

<400> SEQUENCE: 131
cgatcggcat tccgcgcttt gagatcacgt atgcgatcg                          39

<210> SEQ ID NO 132
<211> LENGTH: 37
<212> TYPE: DNA
<213> ORGANISM: Artificial Sequence
<220> FEATURE:
<223> OTHER INFORMATION: primer

<400> SEQUENCE: 132
ggcattccgc gcccctttat cacgtatgcg atcgacg                            37

<210> SEQ ID NO 133
<211> LENGTH: 31
<212> TYPE: DNA
<213> ORGANISM: Artificial Sequence
<220> FEATURE:
<223> OTHER INFORMATION: primer

<400> SEQUENCE: 133
ccgcgccccg agtttacgta tgcgatcgac g                                  31

<210> SEQ ID NO 134
<211> LENGTH: 37
<212> TYPE: DNA
<213> ORGANISM: Artificial Sequence
<220> FEATURE:
<223> OTHER INFORMATION: primer

<400> SEQUENCE: 134
ccgcgccccg agatctttta tgcgatcgac gactacg                37

<210> SEQ ID NO 135
<211> LENGTH: 29
<212> TYPE: DNA
<213> ORGANISM: Artificial Sequence
<220> FEATURE:
<223> OTHER INFORMATION: primer

<400> SEQUENCE: 135
ccccgagatc acgtttgcga tcgacgact                29

<210> SEQ ID NO 136
<211> LENGTH: 41
<212> TYPE: DNA
<213> ORGANISM: Artificial Sequence
<220> FEATURE:
<223> OTHER INFORMATION: primer

<400> SEQUENCE: 136
gcgccccgag atcacgtatt ttatcgacga ctacgtgaag c                41

<210> SEQ ID NO 137
<211> LENGTH: 37
<212> TYPE: DNA
<213> ORGANISM: Artificial Sequence
<220> FEATURE:
<223> OTHER INFORMATION: primer

<400> SEQUENCE: 137
ccgagatcac gtatgcgttt gacgactacg tgaagcg                37

<210> SEQ ID NO 138
<211> LENGTH: 39
<212> TYPE: DNA
<213> ORGANISM: Artificial Sequence
<220> FEATURE:
<223> OTHER INFORMATION: primer

<400> SEQUENCE: 138
cgagatcacg tatgcgatct ttgactacgt gaagcgcgg                39

<210> SEQ ID NO 139
<211> LENGTH: 39
<212> TYPE: DNA
<213> ORGANISM: Artificial Sequence
<220> FEATURE:
<223> OTHER INFORMATION: primer

<400> SEQUENCE: 139
gatcacgtat gcgatcgact tttacgtgaa gcgcggcgc                39

<210> SEQ ID NO 140
<211> LENGTH: 33
<212> TYPE: DNA
<213> ORGANISM: Artificial Sequence
<220> FEATURE:
<223> OTHER INFORMATION: primer

<400> SEQUENCE: 140
gtatgcgatc gacgactttg tgaagcgcgg cgc                33

<210> SEQ ID NO 141
<211> LENGTH: 31

```
<212> TYPE: DNA
<213> ORGANISM: Artificial Sequence
<220> FEATURE:
<223> OTHER INFORMATION: primer

<400> SEQUENCE: 141
gcgatcgacg actactttaa gcgcggcgcc g                          31

<210> SEQ ID NO 142
<211> LENGTH: 33
<212> TYPE: DNA
<213> ORGANISM: Artificial Sequence
<220> FEATURE:
<223> OTHER INFORMATION: primer

<400> SEQUENCE: 142
cgatcgacga ctacgtgttt cgcggcgccg cgc                        33

<210> SEQ ID NO 143
<211> LENGTH: 35
<212> TYPE: DNA
<213> ORGANISM: Artificial Sequence
<220> FEATURE:
<223> OTHER INFORMATION: primer

<400> SEQUENCE: 143
tcgacgacta cgtgaagttt ggcgccgcgc atacg                      35

<210> SEQ ID NO 144
<211> LENGTH: 33
<212> TYPE: DNA
<213> ORGANISM: Artificial Sequence
<220> FEATURE:
<223> OTHER INFORMATION: primer

<400> SEQUENCE: 144
cgactacgtg aagcgctttg ccgcgcatac gcg                        33

<210> SEQ ID NO 145
<211> LENGTH: 33
<212> TYPE: DNA
<213> ORGANISM: Artificial Sequence
<220> FEATURE:
<223> OTHER INFORMATION: primer

<400> SEQUENCE: 145
tacgtgaagc gcggctttgc gcatacgcgc gag                        33

<210> SEQ ID NO 146
<211> LENGTH: 33
<212> TYPE: DNA
<213> ORGANISM: Artificial Sequence
<220> FEATURE:
<223> OTHER INFORMATION: primer

<400> SEQUENCE: 146
tgaagcgcgg cgcctttcat acgcgcgagg tct                        33

<210> SEQ ID NO 147
<211> LENGTH: 27
<212> TYPE: DNA
<213> ORGANISM: Artificial Sequence
<220> FEATURE:
<223> OTHER INFORMATION: primer

<400> SEQUENCE: 147
```

-continued

```
gcggcgccgc gtttacgcgc gaggtct                                              27

<210> SEQ ID NO 148
<211> LENGTH: 31
<212> TYPE: DNA
<213> ORGANISM: Artificial Sequence
<220> FEATURE:
<223> OTHER INFORMATION: primer

<400> SEQUENCE: 148
cggcgccgcg cattttcgcg aggtctacgc g                                         31

<210> SEQ ID NO 149
<211> LENGTH: 33
<212> TYPE: DNA
<213> ORGANISM: Artificial Sequence
<220> FEATURE:
<223> OTHER INFORMATION: primer

<400> SEQUENCE: 149
ggcgccgcgc atacgtttga ggtctacgcg acc                                       33

<210> SEQ ID NO 150
<211> LENGTH: 33
<212> TYPE: DNA
<213> ORGANISM: Artificial Sequence
<220> FEATURE:
<223> OTHER INFORMATION: primer

<400> SEQUENCE: 150
gccgcgcata cgcgctttgt ctacgcgacc gcc                                       33

<210> SEQ ID NO 151
<211> LENGTH: 29
<212> TYPE: DNA
<213> ORGANISM: Artificial Sequence
<220> FEATURE:
<223> OTHER INFORMATION: primer

<400> SEQUENCE: 151
gcatacgcgc gagttttacg cgaccgccg                                            29

<210> SEQ ID NO 152
<211> LENGTH: 27
<212> TYPE: DNA
<213> ORGANISM: Artificial Sequence
<220> FEATURE:
<223> OTHER INFORMATION: primer

<400> SEQUENCE: 152
acgcgcgagg tctttgcgac cgccgcg                                              27

<210> SEQ ID NO 153
<211> LENGTH: 35
<212> TYPE: DNA
<213> ORGANISM: Artificial Sequence
<220> FEATURE:
<223> OTHER INFORMATION: primer

<400> SEQUENCE: 153
cgatccgaac catcacttta cgggctcgac gatca                                     35

<210> SEQ ID NO 154
<211> LENGTH: 39
<212> TYPE: DNA
<213> ORGANISM: Artificial Sequence
```

```
<220> FEATURE:
<223> OTHER INFORMATION: primer

<400> SEQUENCE: 154
cgatccgaac catcacatct ttggctcgac gatcatggg                    39

<210> SEQ ID NO 155
<211> LENGTH: 39
<212> TYPE: DNA
<213> ORGANISM: Artificial Sequence
<220> FEATURE:
<223> OTHER INFORMATION: primer

<400> SEQUENCE: 155
tccgaaccat cacatcacgt tttcgacgat catgggcgc                    39

<210> SEQ ID NO 156
<211> LENGTH: 33
<212> TYPE: DNA
<213> ORGANISM: Artificial Sequence
<220> FEATURE:
<223> OTHER INFORMATION: primer

<400> SEQUENCE: 156
catcacatca cgggctttac gatcatgggc gcc                          33

<210> SEQ ID NO 157
<211> LENGTH: 37
<212> TYPE: DNA
<213> ORGANISM: Artificial Sequence
<220> FEATURE:
<223> OTHER INFORMATION: primer

<400> SEQUENCE: 157
atcacatcac gggctcgttt atcatgggcg ccgatgc                      37

<210> SEQ ID NO 158
<211> LENGTH: 29
<212> TYPE: DNA
<213> ORGANISM: Artificial Sequence
<220> FEATURE:
<223> OTHER INFORMATION: primer

<400> SEQUENCE: 158
cacgggctcg acgtttatgg gcgccgatg                               29

<210> SEQ ID NO 159
<211> LENGTH: 29
<212> TYPE: DNA
<213> ORGANISM: Artificial Sequence
<220> FEATURE:
<223> OTHER INFORMATION: primer

<400> SEQUENCE: 159
cgggctcgac gatctttggc gccgatgcg                               29

<210> SEQ ID NO 160
<211> LENGTH: 33
<212> TYPE: DNA
<213> ORGANISM: Artificial Sequence
<220> FEATURE:
<223> OTHER INFORMATION: primer

<400> SEQUENCE: 160
gggctcgacg atcatgtttg ccgatgcgcg cga                          33
```

```
<210> SEQ ID NO 161
<211> LENGTH: 35
<212> TYPE: DNA
<213> ORGANISM: Artificial Sequence
<220> FEATURE:
<223> OTHER INFORMATION: primer

<400> SEQUENCE: 161
gctcgacgat catgggcttt gatgcgcgcg actcc                              35

<210> SEQ ID NO 162
<211> LENGTH: 29
<212> TYPE: DNA
<213> ORGANISM: Artificial Sequence
<220> FEATURE:
<223> OTHER INFORMATION: primer

<400> SEQUENCE: 162
cgatcatggg cgcctttgcg cgcgactcc                                     29

<210> SEQ ID NO 163
<211> LENGTH: 35
<212> TYPE: DNA
<213> ORGANISM: Artificial Sequence
<220> FEATURE:
<223> OTHER INFORMATION: primer

<400> SEQUENCE: 163
cgatcatggg cgccgatttt cgcgactccg tcgtc                              35

<210> SEQ ID NO 164
<211> LENGTH: 33
<212> TYPE: DNA
<213> ORGANISM: Artificial Sequence
<220> FEATURE:
<223> OTHER INFORMATION: primer

<400> SEQUENCE: 164
tgggcgccga tgcgtttgac tccgtcgtcg aca                                33

<210> SEQ ID NO 165
<211> LENGTH: 33
<212> TYPE: DNA
<213> ORGANISM: Artificial Sequence
<220> FEATURE:
<223> OTHER INFORMATION: primer

<400> SEQUENCE: 165
gcgccgatgc gcgctttcc gtcgtcgaca agg                                 33

<210> SEQ ID NO 166
<211> LENGTH: 31
<212> TYPE: DNA
<213> ORGANISM: Artificial Sequence
<220> FEATURE:
<223> OTHER INFORMATION: primer

<400> SEQUENCE: 166
cgatgcgcgc gactttgtcg tcgacaagga c                                  31

<210> SEQ ID NO 167
<211> LENGTH: 31
<212> TYPE: DNA
<213> ORGANISM: Artificial Sequence
<220> FEATURE:
<223> OTHER INFORMATION: primer
```

<400> SEQUENCE: 167
tgcgcgcgac tcctttgtcg acaaggactg c    31

<210> SEQ ID NO 168
<211> LENGTH: 31
<212> TYPE: DNA
<213> ORGANISM: Artificial Sequence
<220> FEATURE:
<223> OTHER INFORMATION: primer

<400> SEQUENCE: 168
cgcgcgactc cgtctttgac aaggactgcc g    31

<210> SEQ ID NO 169
<211> LENGTH: 33
<212> TYPE: DNA
<213> ORGANISM: Artificial Sequence
<220> FEATURE:
<223> OTHER INFORMATION: primer

<400> SEQUENCE: 169
cgcgactccg tcgtctttaa ggactgccgc acg    33

<210> SEQ ID NO 170
<211> LENGTH: 35
<212> TYPE: DNA
<213> ORGANISM: Artificial Sequence
<220> FEATURE:
<223> OTHER INFORMATION: primer

<400> SEQUENCE: 170
cgactccgtc gtcgactttg actgccgcac gttcg    35

<210> SEQ ID NO 171
<211> LENGTH: 35
<212> TYPE: DNA
<213> ORGANISM: Artificial Sequence
<220> FEATURE:
<223> OTHER INFORMATION: primer

<400> SEQUENCE: 171
ctccgtcgtc gacaagtttt gccgcacgtt cgacc    35

<210> SEQ ID NO 172
<211> LENGTH: 35
<212> TYPE: DNA
<213> ORGANISM: Artificial Sequence
<220> FEATURE:
<223> OTHER INFORMATION: primer

<400> SEQUENCE: 172
cgtcgtcgac aaggactttc gcacgttcga ccatc    35

<210> SEQ ID NO 173
<211> LENGTH: 39
<212> TYPE: DNA
<213> ORGANISM: Artificial Sequence
<220> FEATURE:
<223> OTHER INFORMATION: primer

<400> SEQUENCE: 173
gtcgtcgaca aggactgctt tacgttcgac catccgaac    39

<210> SEQ ID NO 174

```
<211> LENGTH: 39
<212> TYPE: DNA
<213> ORGANISM: Artificial Sequence
<220> FEATURE:
<223> OTHER INFORMATION: primer

<400> SEQUENCE: 174
cgaacctgtt catttcgagc tttgcgacga tgccgaccg                              39

<210> SEQ ID NO 175
<211> LENGTH: 39
<212> TYPE: DNA
<213> ORGANISM: Artificial Sequence
<220> FEATURE:
<223> OTHER INFORMATION: primer

<400> SEQUENCE: 175
cctgttcatt tcgagcagct ttacgatgcc gaccgtcgg                              39

<210> SEQ ID NO 176
<211> LENGTH: 37
<212> TYPE: DNA
<213> ORGANISM: Artificial Sequence
<220> FEATURE:
<223> OTHER INFORMATION: primer

<400> SEQUENCE: 176
tcatttcgag cagcgcgttt atgccgaccg tcggtac                                37

<210> SEQ ID NO 177
<211> LENGTH: 29
<212> TYPE: DNA
<213> ORGANISM: Artificial Sequence
<220> FEATURE:
<223> OTHER INFORMATION: primer

<400> SEQUENCE: 177
gagcagcgcg acgtttccga ccgtcggta                                         29

<210> SEQ ID NO 178
<211> LENGTH: 37
<212> TYPE: DNA
<213> ORGANISM: Artificial Sequence
<220> FEATURE:
<223> OTHER INFORMATION: primer

<400> SEQUENCE: 178
gagcagcgcg acgatgttta ccgtcggtac cgtaaac                                37

<210> SEQ ID NO 179
<211> LENGTH: 37
<212> TYPE: DNA
<213> ORGANISM: Artificial Sequence
<220> FEATURE:
<223> OTHER INFORMATION: primer

<400> SEQUENCE: 179
cagcgcgacg atgccgtttg tcggtaccgt aaacgtg                                37

<210> SEQ ID NO 180
<211> LENGTH: 35
<212> TYPE: DNA
<213> ORGANISM: Artificial Sequence
<220> FEATURE:
<223> OTHER INFORMATION: primer

<400> SEQUENCE: 180
```

```
gcgacgatgc cgacctttgg taccgtaaac gtgac                                35
```

<210> SEQ ID NO 181
<211> LENGTH: 33
<212> TYPE: DNA
<213> ORGANISM: Artificial Sequence
<220> FEATURE:
<223> OTHER INFORMATION: primer

<400> SEQUENCE: 181

```
cgatgccgac cgtctttacc gtaaacgtga cgc                                  33
```

<210> SEQ ID NO 182
<211> LENGTH: 37
<212> TYPE: DNA
<213> ORGANISM: Artificial Sequence
<220> FEATURE:
<223> OTHER INFORMATION: primer

<400> SEQUENCE: 182

```
gatgccgacc gtcggttttg taaacgtgac gctgacg                              37
```

<210> SEQ ID NO 183
<211> LENGTH: 33
<212> TYPE: DNA
<213> ORGANISM: Artificial Sequence
<220> FEATURE:
<223> OTHER INFORMATION: primer

<400> SEQUENCE: 183

```
cgaccgtcgg tacctttaac gtgacgctga cga                                  33
```

<210> SEQ ID NO 184
<211> LENGTH: 37
<212> TYPE: DNA
<213> ORGANISM: Artificial Sequence
<220> FEATURE:
<223> OTHER INFORMATION: primer

<400> SEQUENCE: 184

```
cgaccgtcgg taccgtattt gtgacgctga cgatcgc                              37
```

<210> SEQ ID NO 185
<211> LENGTH: 35
<212> TYPE: DNA
<213> ORGANISM: Artificial Sequence
<220> FEATURE:
<223> OTHER INFORMATION: primer

<400> SEQUENCE: 185

```
cgtcggtacc gtaaacttta cgctgacgat cgccg                                35
```

<210> SEQ ID NO 186
<211> LENGTH: 37
<212> TYPE: DNA
<213> ORGANISM: Artificial Sequence
<220> FEATURE:
<223> OTHER INFORMATION: primer

<400> SEQUENCE: 186

```
gtcggtaccg taaacgtgtt tctgacgatc gccgcgc                              37
```

<210> SEQ ID NO 187
<211> LENGTH: 35
<212> TYPE: DNA

-continued

```
<213> ORGANISM: Artificial Sequence
<220> FEATURE:
<223> OTHER INFORMATION: primer

<400> SEQUENCE: 187
gtaccgtaaa cgtgacgttt acgatcgccg cgctc                                    35

<210> SEQ ID NO 188
<211> LENGTH: 35
<212> TYPE: DNA
<213> ORGANISM: Artificial Sequence
<220> FEATURE:
<223> OTHER INFORMATION: primer

<400> SEQUENCE: 188
ccgtaaacgt gacgctgttt atcgccgcgc tcgcg                                    35

<210> SEQ ID NO 189
<211> LENGTH: 29
<212> TYPE: DNA
<213> ORGANISM: Artificial Sequence
<220> FEATURE:
<223> OTHER INFORMATION: primer

<400> SEQUENCE: 189
acgtgacgct gacgtttgcc gcgctcgcg                                           29

<210> SEQ ID NO 190
<211> LENGTH: 33
<212> TYPE: DNA
<213> ORGANISM: Artificial Sequence
<220> FEATURE:
<223> OTHER INFORMATION: primer

<400> SEQUENCE: 190
cgtgacgctg acgatctttg cgctcgcgct gcg                                      33

<210> SEQ ID NO 191
<211> LENGTH: 33
<212> TYPE: DNA
<213> ORGANISM: Artificial Sequence
<220> FEATURE:
<223> OTHER INFORMATION: primer

<400> SEQUENCE: 191
acgctgacga tcgcctttct cgcgctgcgg atg                                      33

<210> SEQ ID NO 192
<211> LENGTH: 29
<212> TYPE: DNA
<213> ORGANISM: Artificial Sequence
<220> FEATURE:
<223> OTHER INFORMATION: primer

<400> SEQUENCE: 192
gacgatcgcc gcgtttgcgc tgcggatgt                                           29

<210> SEQ ID NO 193
<211> LENGTH: 33
<212> TYPE: DNA
<213> ORGANISM: Artificial Sequence
<220> FEATURE:
<223> OTHER INFORMATION: primer

<400> SEQUENCE: 193
cgatcgccgc gctctttctg cggatgtcgg aca                                      33
```

```
<210> SEQ ID NO 194
<211> LENGTH: 29
<212> TYPE: DNA
<213> ORGANISM: Artificial Sequence
<220> FEATURE:
<223> OTHER INFORMATION: primer

<400> SEQUENCE: 194
gccgcgctcg cgtttcggat gtcggacac                                29

<210> SEQ ID NO 195
<211> LENGTH: 33
<212> TYPE: DNA
<213> ORGANISM: Artificial Sequence
<220> FEATURE:
<223> OTHER INFORMATION: primer

<400> SEQUENCE: 195
ccgcgctcgc gctgtttatg tcggacacgc tga                           33

<210> SEQ ID NO 196
<211> LENGTH: 31
<212> TYPE: DNA
<213> ORGANISM: Artificial Sequence
<220> FEATURE:
<223> OTHER INFORMATION: primer

<400> SEQUENCE: 196
gctcgcgctg cggttttcgg acacgctgaa g                             31

<210> SEQ ID NO 197
<211> LENGTH: 33
<212> TYPE: DNA
<213> ORGANISM: Artificial Sequence
<220> FEATURE:
<223> OTHER INFORMATION: primer

<400> SEQUENCE: 197
tcgcgctgcg gatgtttgac acgctgaaga agg                           33

<210> SEQ ID NO 198
<211> LENGTH: 37
<212> TYPE: DNA
<213> ORGANISM: Artificial Sequence
<220> FEATURE:
<223> OTHER INFORMATION: primer

<400> SEQUENCE: 198
cgcgctgcgg atgtcgttta cgctgaagaa ggaagtc                       37

<210> SEQ ID NO 199
<211> LENGTH: 37
<212> TYPE: DNA
<213> ORGANISM: Artificial Sequence
<220> FEATURE:
<223> OTHER INFORMATION: primer

<400> SEQUENCE: 199
cgcgctgcgg atgtcgatgt ttctgaagaa ggaagtc                       37

<210> SEQ ID NO 200
<211> LENGTH: 37
<212> TYPE: DNA
<213> ORGANISM: Artificial Sequence
<220> FEATURE:
```

<223> OTHER INFORMATION: primer

<400> SEQUENCE: 200
cgcgctgcgg atgtcgatga cgtttaagaa ggaagtc    37

<210> SEQ ID NO 201
<211> LENGTH: 37
<212> TYPE: DNA
<213> ORGANISM: Artificial Sequence
<220> FEATURE:
<223> OTHER INFORMATION: primer

<400> SEQUENCE: 201
cgcgctgcgg atgtcgatga cgctgtttaa ggaagtc    37

<210> SEQ ID NO 202
<211> LENGTH: 37
<212> TYPE: DNA
<213> ORGANISM: Artificial Sequence
<220> FEATURE:
<223> OTHER INFORMATION: primer

<400> SEQUENCE: 202
cgcgctgcgg atgtcgatga cgctgaagtt tgaagtc    37

<210> SEQ ID NO 203
<211> LENGTH: 37
<212> TYPE: DNA
<213> ORGANISM: Artificial Sequence
<220> FEATURE:
<223> OTHER INFORMATION: primer

<400> SEQUENCE: 203
cgcgctgcgg atgtcgatga cgctgaagaa gtttgtc    37

<210> SEQ ID NO 204
<211> LENGTH: 37
<212> TYPE: DNA
<213> ORGANISM: Artificial Sequence
<220> FEATURE:
<223> OTHER INFORMATION: primer

<400> SEQUENCE: 204
cgcgctgcgg atgtcgatga cgctgaagaa ggaattt    37

<210> SEQ ID NO 205
<211> LENGTH: 35
<212> TYPE: DNA
<213> ORGANISM: Artificial Sequence
<220> FEATURE:
<223> OTHER INFORMATION: primer

<400> SEQUENCE: 205
gaagaagatc cacctgggca acctgtcgcg catcg    35

<210> SEQ ID NO 206
<211> LENGTH: 27
<212> TYPE: DNA
<213> ORGANISM: Artificial Sequence
<220> FEATURE:
<223> OTHER INFORMATION: primer

<400> SEQUENCE: 206
aagatccacc tggcgaacct gtcgcgc    27

<210> SEQ ID NO 207
<211> LENGTH: 35
<212> TYPE: DNA
<213> ORGANISM: Artificial Sequence
<220> FEATURE:
<223> OTHER INFORMATION: primer

<400> SEQUENCE: 207
gaagaagatc cacctggtga acctgtcgcg catcg                     35

<210> SEQ ID NO 208
<211> LENGTH: 33
<212> TYPE: DNA
<213> ORGANISM: Artificial Sequence
<220> FEATURE:
<223> OTHER INFORMATION: primer

<400> SEQUENCE: 208
gaagaagatc cacctgctga acctgtcgcg cat                       33

<210> SEQ ID NO 209
<211> LENGTH: 39
<212> TYPE: DNA
<213> ORGANISM: Artificial Sequence
<220> FEATURE:
<223> OTHER INFORMATION: primer

<400> SEQUENCE: 209
gcgaagaaga tccacctgat taacctgtcg cgcatcgac                 39

<210> SEQ ID NO 210
<211> LENGTH: 35
<212> TYPE: DNA
<213> ORGANISM: Artificial Sequence
<220> FEATURE:
<223> OTHER INFORMATION: primer

<400> SEQUENCE: 210
gaagaagatc cacctgatga acctgtcgcg catcg                     35

<210> SEQ ID NO 211
<211> LENGTH: 27
<212> TYPE: DNA
<213> ORGANISM: Artificial Sequence
<220> FEATURE:
<223> OTHER INFORMATION: primer

<400> SEQUENCE: 211
aagatccacc tgccgaacct gtcgcgc                              27

<210> SEQ ID NO 212
<211> LENGTH: 37
<212> TYPE: DNA
<213> ORGANISM: Artificial Sequence
<220> FEATURE:
<223> OTHER INFORMATION: primer

<400> SEQUENCE: 212
gcgaagaaga tccacctgtt taacctgtcg cgcatcg                   37

<210> SEQ ID NO 213
<211> LENGTH: 29
<212> TYPE: DNA
<213> ORGANISM: Artificial Sequence
<220> FEATURE:
<223> OTHER INFORMATION: primer

```
<400> SEQUENCE: 213
agaagatcca cctgtggaac ctgtcgcgc                                      29

<210> SEQ ID NO 214
<211> LENGTH: 35
<212> TYPE: DNA
<213> ORGANISM: Artificial Sequence
<220> FEATURE:
<223> OTHER INFORMATION: primer

<400> SEQUENCE: 214
gaagaagatc cacctgacca acctgtcgcg catcg                               35

<210> SEQ ID NO 215
<211> LENGTH: 37
<212> TYPE: DNA
<213> ORGANISM: Artificial Sequence
<220> FEATURE:
<223> OTHER INFORMATION: primer

<400> SEQUENCE: 215
gcgaagaaga tccacctgaa caacctgtcg cgcatcg                             37

<210> SEQ ID NO 216
<211> LENGTH: 35
<212> TYPE: DNA
<213> ORGANISM: Artificial Sequence
<220> FEATURE:
<223> OTHER INFORMATION: primer

<400> SEQUENCE: 216
gaagaagatc cacctgcaga acctgtcgcg catcg                               35

<210> SEQ ID NO 217
<211> LENGTH: 37
<212> TYPE: DNA
<213> ORGANISM: Artificial Sequence
<220> FEATURE:
<223> OTHER INFORMATION: primer

<400> SEQUENCE: 217
gcgaagaaga tccacctgta taacctgtcg cgcatcg                             37

<210> SEQ ID NO 218
<211> LENGTH: 35
<212> TYPE: DNA
<213> ORGANISM: Artificial Sequence
<220> FEATURE:
<223> OTHER INFORMATION: primer

<400> SEQUENCE: 218
gaagaagatc cacctgtgca acctgtcgcg catcg                               35

<210> SEQ ID NO 219
<211> LENGTH: 39
<212> TYPE: DNA
<213> ORGANISM: Artificial Sequence
<220> FEATURE:
<223> OTHER INFORMATION: primer

<400> SEQUENCE: 219
gcgaagaaga tccacctgaa aaacctgtcg cgcatcgac                           39

<210> SEQ ID NO 220
<211> LENGTH: 35
```

```
<212> TYPE: DNA
<213> ORGANISM: Artificial Sequence
<220> FEATURE:
<223> OTHER INFORMATION: primer

<400> SEQUENCE: 220
gaagaagatc cacctgcgca acctgtcgcg catcg                              35

<210> SEQ ID NO 221
<211> LENGTH: 37
<212> TYPE: DNA
<213> ORGANISM: Artificial Sequence
<220> FEATURE:
<223> OTHER INFORMATION: primer

<400> SEQUENCE: 221
gcgaagaaga tccacctgca taacctgtcg cgcatcg                            37

<210> SEQ ID NO 222
<211> LENGTH: 37
<212> TYPE: DNA
<213> ORGANISM: Artificial Sequence
<220> FEATURE:
<223> OTHER INFORMATION: primer

<400> SEQUENCE: 222
gcgaagaaga tccacctgga taacctgtcg cgcatcg                            37

<210> SEQ ID NO 223
<211> LENGTH: 37
<212> TYPE: DNA
<213> ORGANISM: Artificial Sequence
<220> FEATURE:
<223> OTHER INFORMATION: primer

<400> SEQUENCE: 223
gcgaagaaga tccacctgga aaacctgtcg cgcatcg                            37

<210> SEQ ID NO 224
<211> LENGTH: 41
<212> TYPE: DNA
<213> ORGANISM: Artificial Sequence
<220> FEATURE:
<223> OTHER INFORMATION: primer

<400> SEQUENCE: 224
cgtgttcaac gacgaattcg atccgaacaa tcacatcacg g                       41

<210> SEQ ID NO 225
<211> LENGTH: 41
<212> TYPE: DNA
<213> ORGANISM: Artificial Sequence
<220> FEATURE:
<223> OTHER INFORMATION: primer

<400> SEQUENCE: 225
ccgtgatgtg attgttcgga tcgaattcgt cgttgaacac g                       41

<210> SEQ ID NO 226
<211> LENGTH: 31
<212> TYPE: DNA
<213> ORGANISM: Artificial Sequence
<220> FEATURE:
<223> OTHER INFORMATION: primer

<400> SEQUENCE: 226
```

-continued

```
aattcgcgcc gaaccaccac atcacgggct c                                31

<210> SEQ ID NO 227
<211> LENGTH: 31
<212> TYPE: DNA
<213> ORGANISM: Artificial Sequence
<220> FEATURE:
<223> OTHER INFORMATION: primer

<400> SEQUENCE: 227
gagcccgtga tgtggtggtt cggcgcgaat t                                31
```